US009393195B2

(12) United States Patent
Mizuno et al.

(10) Patent No.: US 9,393,195 B2
(45) Date of Patent: *Jul. 19, 2016

(54) SYSTEMS FOR CARTILAGE REPAIR

(71) Applicant: Histogenics Corporation, Waltham, MA (US)

(72) Inventors: Shuichi Mizuno, Brookline, MA (US); Akihiko Kusanagi, Brookline, MA (US); Laurence J. B. Tarrant, Easthampton, MA (US); Toshimasa Tokuno, Tokyo (JP); Robert Lane Smith, Palo Alto, CA (US)

(73) Assignee: Histogenics Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/899,024

(22) Filed: May 21, 2013

(65) Prior Publication Data

US 2013/0273121 A1  Oct. 17, 2013

Related U.S. Application Data

(63) Continuation of application No. 10/625,245, filed on Jul. 22, 2003, now abandoned, which is a continuation-in-part of application No. 10/104,677, filed on Mar. 22, 2002, now Pat. No. 6,949,252.

(60) Provisional application No. 60/425,696, filed on Nov. 12, 2002, provisional application No. 60/427,627, filed on Nov. 18, 2002.

(51) Int. Cl.
| | | |
|---|---|---|
| A61L 27/24 | (2006.01) | |
| A61L 27/38 | (2006.01) | |
| A61L 27/56 | (2006.01) | |
| A61K 9/00 | (2006.01) | |
| A61L 27/36 | (2006.01) | |
| C12N 5/077 | (2010.01) | |
| A61K 35/32 | (2015.01) | |
| A61K 35/12 | (2015.01) | |

(52) U.S. Cl.
CPC ............... *A61K 9/0024* (2013.01); *A61K 35/32* (2013.01); *A61L 27/24* (2013.01); *A61L 27/3633* (2013.01); *A61L 27/3817* (2013.01); *A61L 27/3843* (2013.01); *A61L 27/3852* (2013.01); *A61L 27/3895* (2013.01); *A61L 27/56* (2013.01); *C12N 5/0655* (2013.01); *A61F 2310/00365* (2013.01); *A61K 35/12* (2013.01); *A61L 2430/06* (2013.01); *C12N 2533/54* (2013.01)

(58) Field of Classification Search
USPC ......... 424/93.7, 423, 400; 435/395, 177, 366, 435/404, 180; 514/17, 7.6
IPC ................ C12N 5/00,5/02; A61L 27/24, 27/38, A61L 27/56; A61K 35/12, 38/18
See application file for complete search history.

(56) References Cited

U.S. PATENT DOCUMENTS

| | | |
|---|---|---|
| 4,182,655 A | 1/1980 | Hartmeier |
| 4,522,753 A | 6/1985 | Yannas et al. |
| 4,851,354 A | 7/1989 | Winston et al. |
| 4,912,032 A | 3/1990 | Hoffman et al. |
| 5,116,824 A | 5/1992 | Miyata et al. |
| 5,206,028 A | 4/1993 | Li |
| 5,656,492 A | 8/1997 | Glowacki et al. |
| 5,723,331 A | 3/1998 | Tubo et al. |
| 5,759,190 A | 6/1998 | Vibe-Hansen et al. |
| 5,786,217 A | 7/1998 | Tubo et al. |
| 5,830,493 A | 11/1998 | Yokota et al. |
| 5,902,741 A | 5/1999 | Purchio et al. |
| 5,928,945 A | 7/1999 | Seliktar et al. |
| 5,972,385 A | 10/1999 | Liu et al. |
| 5,989,269 A | 11/1999 | Vibe-Hansen et al. |
| 6,080,194 A | 6/2000 | Pachence et al. |
| 6,150,163 A | 11/2000 | McPherson et al. |
| 6,156,572 A | 12/2000 | Bellamkonda et al. |
| 6,171,610 B1 | 1/2001 | Vacanti et al. |
| 6,294,202 B1 | 9/2001 | Burns et al. |
| 6,306,169 B1* | 10/2001 | Lee ..................... A61L 27/3804 623/11.11 |

(Continued)

FOREIGN PATENT DOCUMENTS

| | | |
|---|---|---|
| JP | 622744 | 2/1994 |
| WO | WO-9844874 A1 | 10/1998 |

(Continued)

OTHER PUBLICATIONS

Parkkinen et al. 1995. Influence of Short-Term Hydrostatic Pressure on Organization of Stress Fibers in Cultured Chondrocytes. Journal of Orthopaedic Research, vol. 13, No. 5, pp. 495-502.*

(Continued)

*Primary Examiner* — Debbie K Ware
*Assistant Examiner* — Kailash C Srivastava
(74) *Attorney, Agent, or Firm* — Brown Rudnick LLP; Thomas C. Meyers

(57) ABSTRACT

Neo-cartilage constructs suitable for implantation into a joint cartilage lesion in situ and a method for repair and restoration of function of injured, traumatized, aged or diseased cartilage. The construct comprises at least chondrocytes incorporated into a support matrix processed according to the algorithm comprising variable hydrostatic or atmospheric pressure or non-pressure conditions, variable rate of perfusion, variable medium composition, variable temperature, variable cell density and variable time to which the chondrocytes are subjected.

8 Claims, 14 Drawing Sheets

(56) References Cited

U.S. PATENT DOCUMENTS

| | | | |
|---|---|---|---|
| 6,312,725 | B1 | 11/2001 | Wallace et al. |
| 6,322,563 | B1 | 11/2001 | Cummings et al. |
| 6,432,713 | B2 | 8/2002 | Takagi et al. |
| 6,511,958 | B1* | 1/2003 | Atkinson et al. ............. 424/94.4 |
| 6,528,052 | B1* | 3/2003 | Smith et al. .................. 424/93.7 |
| 6,632,651 | B1 | 10/2003 | Nevo et al. |
| 6,652,872 | B2 | 11/2003 | Nevo et al. |
| 6,893,466 | B2* | 5/2005 | Trieu ........................ 623/17.16 |
| 6,949,252 | B2* | 9/2005 | Mizuno et al. ................ 424/423 |
| 6,991,652 | B2* | 1/2006 | Burg ............................... 623/8 |
| 7,025,916 | B2 | 4/2006 | Bachrach |
| 7,148,209 | B2 | 12/2006 | Hoemann et al. |
| 7,157,428 | B2* | 1/2007 | Kusanagi et al. ............. 424/484 |
| 7,208,177 | B2* | 4/2007 | Geistlich et al. ............. 424/484 |
| 7,217,294 | B2* | 5/2007 | Kusanagi et al. .......... 623/18.11 |
| 7,468,192 | B2* | 12/2008 | Mizuno et al. ................ 424/423 |
| 7,537,780 | B2* | 5/2009 | Mizuno et al. ................ 424/423 |
| 8,070,827 | B2 | 12/2011 | Shortkroff |
| 8,685,107 | B2 | 4/2014 | Claesson et al. |
| 8,906,686 | B2* | 12/2014 | Mizuno et al. ................ 435/395 |
| 8,921,109 | B2* | 12/2014 | Smith et al. .................. 435/395 |
| 9,149,562 | B2 | 10/2015 | Shortkroff et al. |
| 2001/0021529 | A1 | 9/2001 | Takagi |
| 2001/0055615 | A1 | 12/2001 | Wallace et al. |
| 2002/0082220 | A1 | 6/2002 | Hoemann et al. |
| 2002/0082623 | A1 | 6/2002 | Osther et al. |
| 2002/0106625 | A1 | 8/2002 | Hung et al. |
| 2002/0115208 | A1* | 8/2002 | Mitchell et al. ............... 435/325 |
| 2005/0186685 | A1 | 8/2005 | Kange et al. |
| 2006/0286144 | A1 | 12/2006 | Yang et al. |
| 2007/0065943 | A1 | 3/2007 | Smith et al. |
| 2008/0031923 | A1 | 2/2008 | Murray et al. |
| 2008/0260801 | A1 | 10/2008 | Ahlers et al. |
| 2009/0012628 | A1 | 1/2009 | Shortkroff et al. |
| 2014/0193468 | A1* | 7/2014 | Tarrant et al. ................. 424/400 |

FOREIGN PATENT DOCUMENTS

| | | |
|---|---|---|
| WO | 00/31130 A1 | 6/2000 |
| WO | WO-0102030 A2 | 1/2001 |

OTHER PUBLICATIONS

European Search Report and Opinion for EP11190811.7 dated Feb. 14, 2012, 10 pages.

International Preliminary Examination Report for PCT/US02/09001 dated Oct. 30, 2004, 7 pages.

International Search Report for PCT/US02/09001 dated Mar. 27, 2003, 2 pages.

Richard W. Farndale, et al., A Direct Spectrophotometric Microassay For Sulfated Glycosaminoglycans in Cartilage Cultures, Connective Tissue Research, 9:247-248 (1982).

Smith, R., et al,. "In vitro stimulation of articular chondrocyte mRNA and extracellular matrix synthesis by hydrostatic pressure," Journal of Orthopaedic Research, John Wiley & Sons, Inc., Needham, MA, vol. 14, No. 1, Jan. 1, 1996, pp. 53-60, XP002961860 ISSN: 0736-0266.

Supplementary European Search Report for EP02753826 dated Jul. 17, 2009, 2 pages.

Abraham, 1986, Human basic fibroblast growth factor: nucleotide sequence and genomic organization, EMBO J 5(10):2523-2528.

Fujisato, 1996, Effect of basic fibroblast growth on cartilage regeneration in chondrocyte-seeded collagen sponge scaffold, Biomaterials 17:155-162.

Venkataraman, 1999, Molecular characteristics of fibroblast growth factor—fibroblast growth factor receptor—heparin-ike glycosaminoglycan complex, PNAS 96:3658-3663.

Parkkinen, 1995, Influence of short-term hydrostatic pressure on organization of stress fibers in cultured chondrocytes, J Orth Res 13(5):495-502.

* cited by examiner

- Hydrostatic static pressure
- Medium flow rate
- Gas concentration
- Temperature setting Mean±SD (*p<0.05)

*: S-GAG accumulation        Collagen sponge

Mean+SD (*: p<0.05)

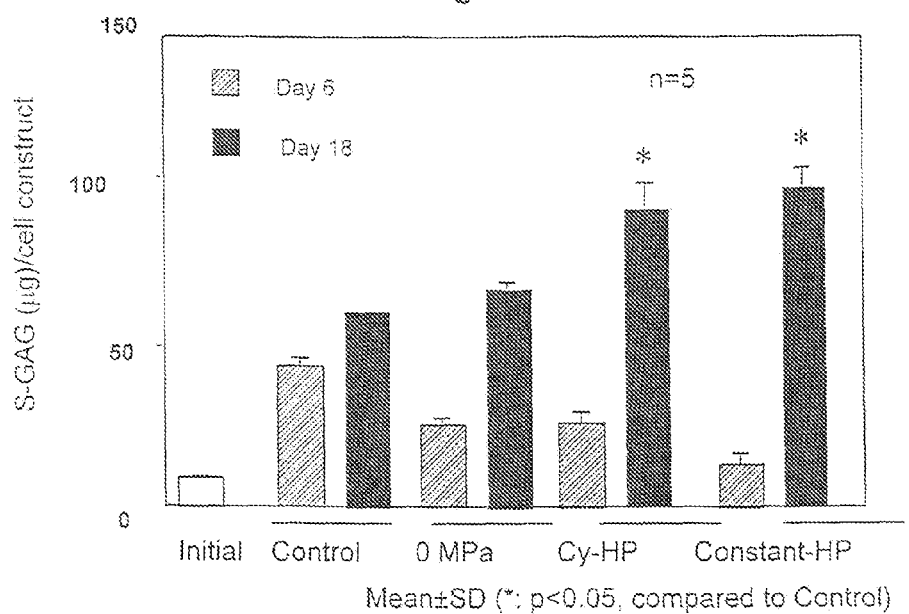
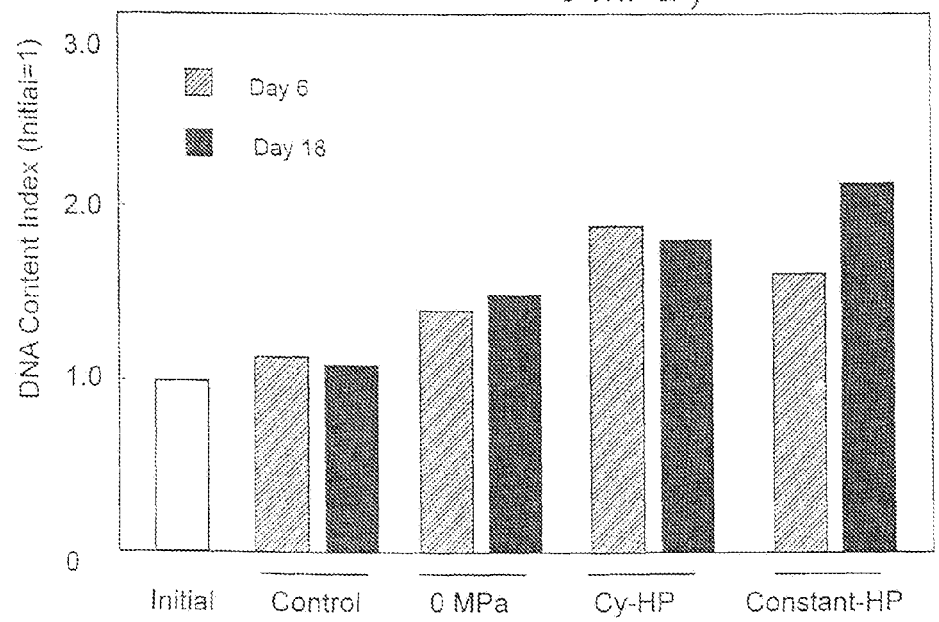

Fig. 6A
Fig. 6B
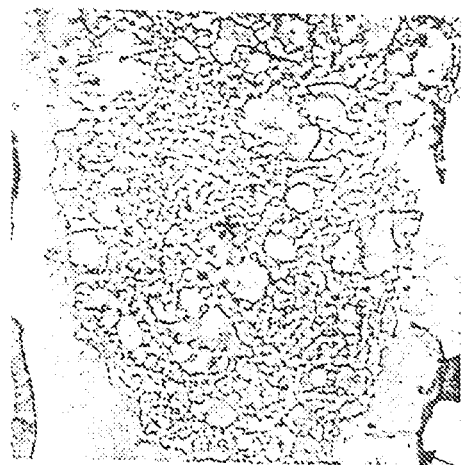
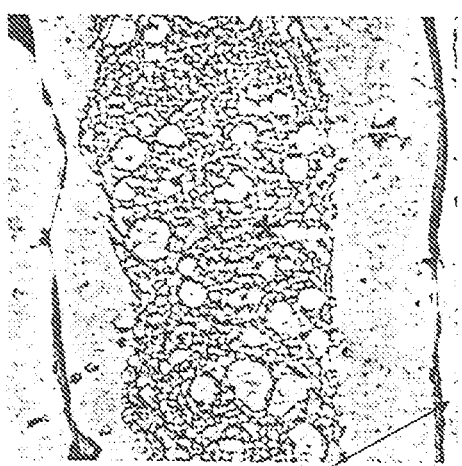
*: S-GAG accumulation (Day 18)    Collagen sponge
Fig. 6C
Fig. 6D
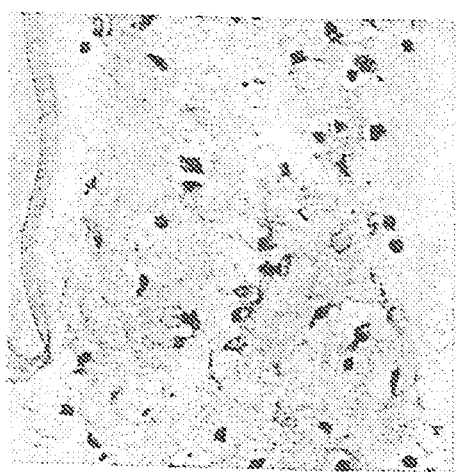
*: Type II collagen accumulation (Day 6)

Mean±SD (*: p<0.05)

Mean±SD(*: P<0.05)

H: Host cartilage, D: Defect site, SB: Subchondral bone

H: Host cartilage, D: Defect site, SB: Subchondral bone, SY: Synovium

H: Host cartilage, D: Defect site, SB: Subchondral bone

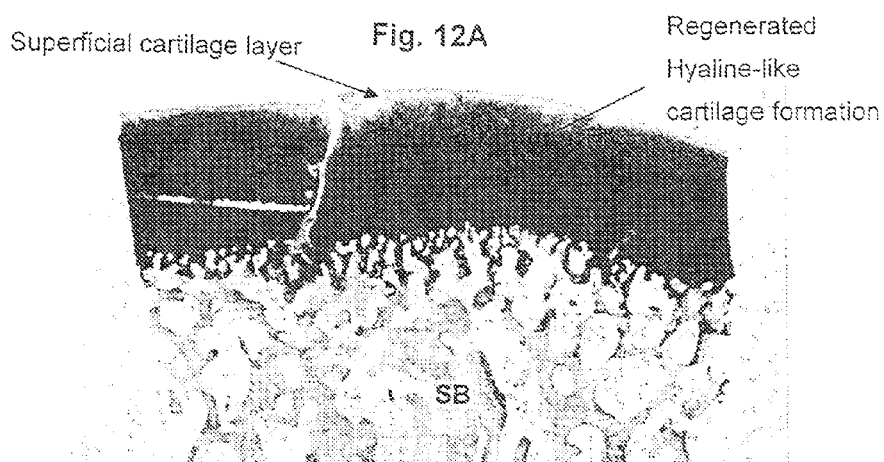
H: Host cartilage, N: Porcine-NeoCart™ implant site, SB: Subchondral bone
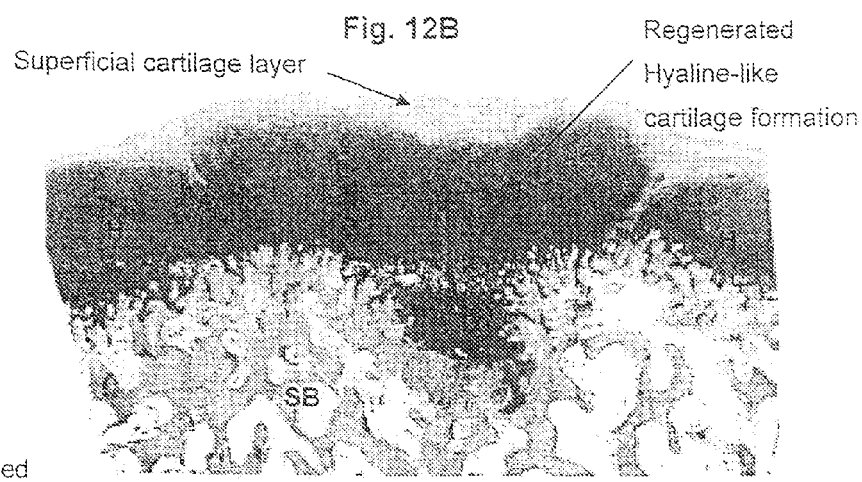
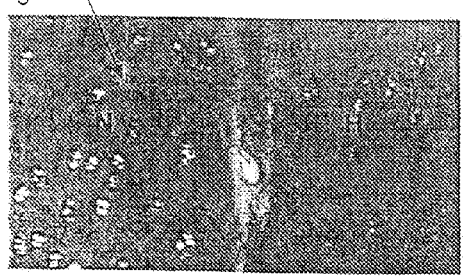
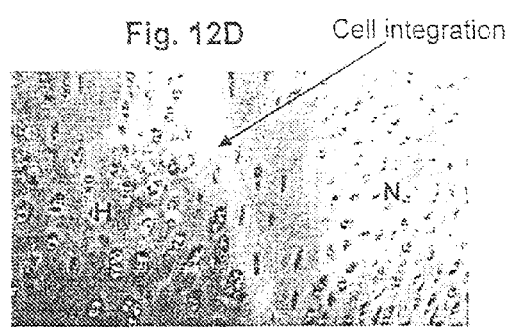

SYSTEMS FOR CARTILAGE REPAIR

RELATED APPLICATIONS

This application is a continuation of U.S. Ser. No. 10/625,245, filed on Jul. 22, 2003, which is a continuation-in-part application of U.S. Ser. No. 10/104,677, filed on Mar. 22, 2002, now U.S. Pat. No. 6,949,252, and is based on and claims priority to U.S. Provisional application Ser. No. 60/425,696 filed on Nov. 12, 2002 and U.S. Provisional application Ser. No. 60/427,627 filed on Nov. 18, 2002.

FIELD OF INVENTION

The current invention concerns neo-cartilage constructs suitable for implantation into a joint cartilage lesion in situ and a method for repair and restoration of function of injured, traumatized, aged or diseased cartilage. The construct of the invention comprises at least chondrocytes incorporated into a support matrix processed according to the algorithm of the invention. In particular, the invention concerns a neo-cartilage construct for in situ implanting into a cartilage lesion wherein said construct comprises a cultured differentiated autologous or heterologous chondrocytes or cells which could be differentiated into chondrocytes incorporated into a support matrix and subjected to an algorithm of the invention wherein said algorithm comprises variable hydrostatic or atmospheric pressure or non-pressure conditions, variable rate of perfusion, variable medium composition, variable temperature, variable concentration of oxygen or other gases, variable cell density and variable time to which the chondrocytes are subjected.

Additionally, the invention concerns a method for generation of the neo-cartilage and the neo-cartilage construct of the invention.

The invention further concerns a method where the implantation of the construct of the invention initiates and achieves incorporation of the neo-cartilage into a native surrounding cartilage. The construct is implanted into the joint cartilage lesion typically below one layer or between two layers of biologically acceptable sealants.

The invention further concerns a method for repair and restoration of the injured, damaged, diseased or aged cartilage into its full functionality and for treatment of injured or diseased cartilage by implanting the neo-cartilage construct between two layers of biologically acceptable sealants.

BACKGROUND AND RELATED DISCLOSURES

Damage to the articular cartilage which occurs in active individuals and older generation adults as a result of either acute or repetitive traumatic injury or aging is quite common. Such damaged cartilage leads to pain, affects mobility and results in debilitating disability.

Typical treatment choices, depending on lesion and symptom severity, are rest and other conservative treatments, minor arthroscopic surgery to clean up and smooth the surface of the damaged cartilage area, and other surgical procedures such as microfracture, drilling, and abrasion. All of these may provide symptomatic relief, but the benefit is usually only temporary, especially if the person's pre-injury activity level is maintained. For example, severe and chronic forms of knee joint cartilage damage can lead to greater deterioration of the joint cartilage and may eventually lead to a total knee joint replacement. Approximately 200,000 total knee replacement operations are performed annually. The artificial joint generally lasts only 10 to 15 years and the operation is, therefore, typically not recommended for people under the age of fifty.

It would, therefore, be extremely advantageous to have available a method for in situ treatment of these injuries which would effectively restore the cartilage to its pre-injury state.

Attempts to provide means and methods for repair of articular cartilage are disclosed, for example, in U.S. Pat. Nos. 5,723,331; 5,786,217; 6,150,163; 6,294,202; 6,322,563 and in the U.S. patent application Ser. No. 09/896,912, filed on Jun. 29, 2001.

U.S. Pat. No. 5,723,331 describes methods and compositions for preparation of synthetic cartilage for the repair of articular cartilage using ex vivo proliferated denuded chondrogenic cells seeded ex vivo, in the wells containing adhesive surface. These cells redifferentiate and begin to secrete cartilage-specific extracellular matrix thereby providing an unlimited amount of synthetic cartilage for surgical delivery to a site of the articular defect.

U.S. Pat. No. 5,786,217 describes methods for preparing a multi-cell layered synthetic cartilage patch prepared essentially by the same method as described in '331 patent except that the denuded cells are non-differentiated, and culturing these cells for a time necessary for these cells to differentiate and form a multi cell-layered synthetic cartilage.

U.S. application Ser. No. 09/896,912, filed on Jun. 29, 2001 concerns a method for repairing cartilage, meniscus, ligament, tendon, bone, skin, cornea, periodontal tissues, abscesses, resected tumors and ulcers by introducing into tissue a temperature dependent polymer gel in conjunction with at least one blood component which adheres to the tissue and promotes support for cell proliferation for repairing the tissue.

None of the above cited references results in repair and regeneration of cartilage in situ including de novo formation of the superficial cartilage layer sealing a joint cartilage lesion in situ.

It is thus a primary objective of this invention to provide a method and means for regeneration of injured or traumatized cartilage by forming, in the injured lesion of the cartilage, a cavity, by administering at least one but typically two separate layers of a biologically acceptable glue sealant and implanting a neo-cartilage containing construct under the one layer or into said cavity. The method according to the invention results in the growth of the superficial cartilage layer over the lesion and sealing the lesion.

All patents, patent applications and publications cited herein are hereby incorporated by reference.

SUMMARY

One aspect of the current invention is a neo-cartilage construct suitable for implantation into a cartilage lesion in situ.

Another aspect of the current invention is a neo-cartilage construct implanted under one or between two layers of biologically acceptable sealants within a cartilage lesion.

Another aspect of the current invention is a method for fabrication of a three-dimensional neo-cartilage construct of the invention comprising steps of:

a) preparing a support matrix structure;
b) harvesting a piece of cartilage from a donor for isolation of chondrocytes;
c) culturing and expanding the chondrocytes;
d) suspending the expanded chondrocytes in a suspension fluid;
e) incorporating said suspended chondrocytes into said matrix; and f) propagating said chondrocytes into two or three-dimensional neo-cartilage construct using the algorithm of the invention.

Still another aspect of the current invention is a method for generation of an autologous type of neo-cartilage construct by generating a carrier support for autologous chondrocytes cultured into neo-cartilage wherein said support is a biologically acceptable cell-carrier thermo-reversible polymer gel or a thermo-reversible gelation hydrogel (CCTG, TRGH or VITROGEN®), wherein said neo-cartilage is suspended within the CCTG and wherein a resulting CCTG/neo-cartilage or TRGH/neo-cartilage or a suspension thereof is injected into the cartilage lesion.

Still another aspect of the current invention is a neo-cartilage construct implanted in situ into a cartilage lesion between two layers of sealants wherein a first sealant is deposited at the bottom of a cartilage lesion and the second sealant is deposited over the implanted construct on the top of the cartilage lesion and wherein the second sealant leads to formation and growth of superficial cartilage layer which seals said cartilage lesion.

Another aspect of the current invention is a method for repair and restoration of damaged, injured, diseased or aged cartilage to a functional cartilage, said method comprising steps:

a) preparing a neo-cartilage construct comprising autologous or heterologous chondrocytes incorporated into a sponge, porous scaffold or thermo-reversible gelation hydrogel (TRGH) matrix support and subjected to the algorithm of the invention;

b) optionally introducing a first layer of a first biologically acceptable sealant into a cartilage lesion;

c) implanting said construct into said lesion or into said cavity over the first layer of said first sealant;

d) introducing a second layer of a second biologically acceptable sealant over said construct wherein said second sealant may or may not be the same as the first sealant and wherein a combination of said construct and said second sealant results in formation and growth of a superficial cartilage layer sealing the cartilage lesion in situ.

Another aspect of the current invention is a method for repair and restoration of damaged, injured, diseased or aged cartilage to a functional cartilage, said method comprising steps:

a) obtaining autologous or heterologous chondrocytes;

b) culturing said chondrocytes ex vivo into a neo-cartilage, said neo-cartilage comprising autologous or heterologous chondrocytes incorporated into a sponge or TRGH matrix support subjected to the algorithm of the invention;

c) optionally introducing a first layer of a first biologically acceptable sealant into a cartilage lesion;

d) depositing a space-holding thermo-reversible gel (SHTG) or TRGH into a lesion or into a cavity formed above the first sealant layer thereby permitting sufficient time for growth and differentiation of ex vivo cultured neo-cartilage, said space holding thermo-reversible gel (SHTG) deposited into said cavity as a sol at temperatures between about 5 to about 25° C., wherein within said cavity and at the body temperature said SHTG converts from the fluidic sol into a solid gel and in this form SHTG holds the space for subsequent introduction of the neo-cartilage cultured ex vivo, and provides protection against cell and blood-borne agents migration into the cavity from the subchondral space and from the synovial capsule and wherein its presence further provides a substrate for and promotes in situ formation of a de novo superficial cartilage layer covering the cartilage lesion;

e) depositing a second layer of a second biologically acceptable sealant over the cartilage lesion;

f) removing said SHTG by cooling said lesion to change SHTG into sol;

f) depositing said neo-cartilage cultured ex vivo into the cavity formed between two layers of sealants and under the de novo formed superficial cartilage layer;

g) removing said SHTG or TRGH from the cavity after the neo-cartilage integration into a native cartilage under the formed superficial cartilage layer by cooling said lesion to from about 5 to about 15° C. to convert the solid gel into fluidic sol and removing said sol or, in alternative, leaving said SHTG or TRGH to disintegrate and be removed naturally.

Another aspect of the current invention is a method for repair and restoration of damaged, injured, diseased or aged cartilage to a functional cartilage, said method comprising steps:

a) preparing an intact and discreet piece of neo-cartilage by culturing autologous or heterologous chondrocytes ex vivo, suspending said cultured chondrocytes in a thermo-reversible gelation hydrogel (TRGH) and warming said suspension of chondrocytes to temperature above 30° C. in order to convert TRGH into a solid gel and subjecting the solid gel to the algorithm of the invention;

b) introducing a first and a second layer of a first and a second biologically acceptable sealant into a cartilage lesion;

c) cooling said TRGH/neo-cartilage to 5-15° C. to sol state;

d) depositing said neo-cartilage suspended in the TRGH into a cavity formed between two layers of sealants as a sol at temperatures between about 5 to about 25° C. wherein, within said cavity and at the body temperature, said TRGH converts from the sol state into the solid gel and in this state provides protection for and enables integration of deposited neo-cartilage into a native surrounding cartilage and wherein the presence of TRGH further provides a substrate and promotes in situ formation of de novo superficial cartilage layer covering the cartilage lesion; and e) leaving said TRGH in the lesion until its disintegration or, in alternative, removing said TRGH from the cavity as a sol by cooling said lesion to temperature between 5 and 15° C. after the neo-cartilage integration and formation of superficial cartilage layer.

Another aspect of the current invention is a method for repair and restoration of damaged, injured, diseased or aged cartilage to a functional cartilage, said method comprising steps:

a) preparing neo-cartilage or a neo-cartilage containing construct comprising autologous cultured chondrocytes incorporated into a gel or thermo-reversible gel matrix support ex vivo and subjected to the algorithm of the invention;

b) introducing a first layer of a first biologically acceptable sealant into a cartilage lesion;

c) depositing said construct or said neo-cartilage over the first layer of the first sealant; and d) depositing a layer of a second biologically acceptable sealant either over the neo-cartilage construct or the neo-cartilage deposited into a cartilage lesion and covering the lesion with said second sealant, wherein in time said neo-cartilage is integrated into the native cartilage and wherein the presence of the neo-cartilage construct and the second sealant promotes in situ formation and growth of de novo superficial cartilage layer covering the cartilage lesion.

Still another aspect of the current invention is a method for generation and maintaining integrity of the lesion cavity for the introduction of neo-cartilage, a neo-cartilage gel, a neo-cartilage suspension or neo-cartilage construct from a synovial capsule and for blocking the migration of subchondral and synovial cells and cell and blood products into said cavity and for providing a substrate for a formation of superficial cartilage layer overgrowing the lesion by introducing a biologically acceptable space-holding thermo-reversible gel (SHTG) into a cleaned lesion for a duration of culturing autologous chondrocytes into neo-cartilage before introducing said neo-cartilage or neo-cartilage construct or suspension into the lesion.

Still another aspect of the current invention is a method for treatment of damaged, injured, diseased or aged cartilage by utilizing any of the methods listed above to implant the neo-cartilage construct into the lesion.

BRIEF DESCRIPTION OF DRAWINGS

FIG. 1 shows a construct comprising neo-cartilage.

FIG. 5A shows S-GAG accumulation in cell constructs under continued culture conditions of static culture (control), medium perfusion (COMPa), cyclic hydrostatic pressure (Cy-HP) combined with medium perfusion (control) and constant hydrostatic pressure combined with medium perfusion (constant-HP). FIG. 5B illustrates DNA content at day 6 and day 18 in cells constructs submitted to static conditions (control), medium perfusion only (COMPa), cyclic hydrostatic pressure (Cy-HP) and constant hydrostatic pressure (constant-HP).

FIG. 6A is a photomicrograph of Safranin-O staining for S-GAG on paraffin sections in 18 days cell constructs subjected to static atmospheric pressure. FIG. 6B is a photomicrograph of Safranin-O staining for S-GAG on paraffin sections in cell constructs subjected to cyclic hydrostatic pressure for 6 days followed by 12 days of static pressure. FIG. 6C is a photomicrograph of type II collagen immunohistochemistry on paraffin sections in 6 days cell constructs subjected to static atmospheric pressure. FIG. 6D is a photomicrograph of type II collagen immunohistochemistry on paraffin sections in cell constructs subjected to cyclic hydrostatic pressure for 6 days.

FIG. 11 shows the control lesion without treatment with porcine neo-cartilage where the proliferation of fibrocartilage within the defect site is clearly visible after 4 months.

FIGS. 12A and 12B shows integration of porcine neo-cartilage into the lesion within the host's cartilage after 3 months. FIG. 12C shows the regenerated hyaline-like cartilage in the porcine neo-cartilage implanted site. FIG. 12D shows the integration between the porcine neo-cartilage and the host cartilage laterally and at the subchondral bone.

FIG. 14 shows histological evaluation of cell constructs by Safranin-O.

DEFINITIONS

Figure 1A:
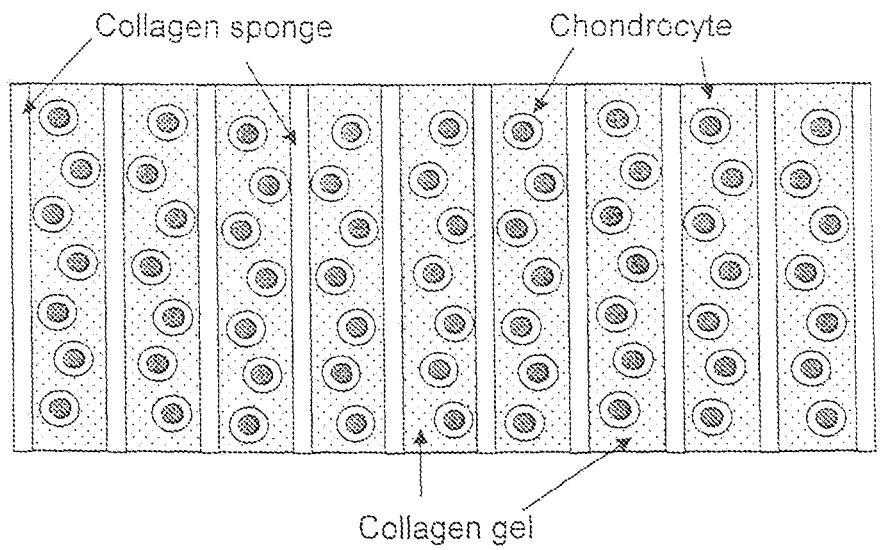
FIG. 1A is a schematic drawing of the sponge made of sol/gel showing the distribution of chondrocytes within the collagen sponge.

As used herein:

"Chondrocyte" means a nondividing cartilage cell which occupies a lacuna within the cartilage matrix.

"Isogenous chondrocytes" means clones of cartilage cell derived from one cell of division. Isogenous chondrocytes occur in clusters called isogenous nests.

"Autologous chondrocytes" means chondrocytes isolated from a donor's own healthy articular cartilage.

"Heterologous chondrocytes" means chondrocytes derived from a donor of a different species or from a donor of the same species but not the recipient individual or a donor tissue that is derived from the recipient individual but is non-articular cartilage isolated from a cartilage of the different species.

"Support matrix" means biologically acceptable sol-gel or sponge scaffold suitable for seeding expanded chondrocytes that provides a structural support for growth and three-dimensional propagation of chondrocytes. The support matrix is prepared from such materials as Type I collagen, Type II collagen, Type IV collagen, gelatin, agarose, cell-contracted collagen containing proteoglycans, glycosaminoglycans or glycoproteins, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel. The support matrix is preferably biocompatible, biodegradable, hydrophilic, non-reactive, has a neutral charge and be able to have or has a defined structure.

"Neo-cartilage" means an immature hyaline cartilage wherein the ratio of extracellular matrix to chondrocytes is lower than in mature hyaline cartilage.

"Mature hyaline cartilage" means cartilage consisting of groups of isogenous chondrocytes located within lacunae cavities which are scattered throughout an extracellular collagen matrix.

"Autologous Cultured Neo-Cartilage" means a hyaline neo-cartilage tissue grown ex vivo from chondrocytes isolated from a donor's own healthy articular cartilage.

"Neo-cartilage construct", "NEOCART™" or "Neo-Cart™" means a 3-dimensional structural composition comprising chondrocytes incorporated into a matrix support treated by or subjected to the algorithm of the invention. Neo-cartilage construct thus means a discrete piece of hyaline neo-cartilage formed from cultured chondrocytes for implantation into lesion of a damaged, aged or diseased cartilage wherein, after implantation, the neo-cartilage is integrated into a native cartilage within the lesion. NeoCart® cartilage is manufactured by and is proprietary of Histogenics Corporation, Easthampton, Mass.

"TESS™" means Tissue Engineering Support System which is available as TESS culture processor unit for culturing of chondrocytes prepared from arthroscopic biopsy samples. The unit permits changes in hydrostatic pressure, including cyclic hydrostatic pressure changes and controls other physical parameters such as temperature, gas concentration, medium perfusion rate and such other parameters as may be needed. Relevant detailed information is found in U.S. Pat. No. 6,432,713 B2, patent application Ser. No. 09/895,162, Ser. No. 09/895,161, PCT JP01/01516, Japanese patent applications 2001-126543 and 2001-261556, incorporated herein by reference.

"Sealant" means a biologically acceptable typically rapid-gelling formulation having a specified range of adhesive and cohesive properties. Sealant is thus a biologically acceptable rapidly gelling synthetic compound having adhesive and/or gluing properties, and is typically a hydrogel, such as derivatized polyethylene glycol (PEG) which is preferably cross-linked with a collagen compound, typically alkylated collagen. Examples of suitable sealants are tetra-hydrosuccinimidyl or tetra-thiol derivatized PEG, or a combination thereof, commercially available from Cohesion Technologies, Palo Alto, Calif. under the trade name CoSeal™, described in *J. Biomed. Mater. Res Appl. Biomater.,* 58:545-555 (2001), or two-part polymer compositions that rapidly form a matrix where at least one of the compounds is polymeric, such as, polyamino acid, polysaccharide, polyalkylene oxide or polyethylene glycol and two parts are linked through a covalent bond, as described in U.S. Pat. No. 6,312,725B1, herein incorporated by reference, and cross-linked PEG with methyl collagen, such as a cross-linked polyethylene glycol hydrogel with methyl-collagen. The sealant of the invention typically gels and/or bonds rapidly upon contact with tissue, particularly with tissue containing collagen.

"First sealant" means a biologically acceptable tissue sealant which is deposited at the bottom of the lesion.

"Second sealant" means a biologically acceptable sealant which is deposited above and over the neo-cartilage construct implanted into a lesion. The second sealant may or may not be the same as the first sealant and is preferably a cross-linked polyethylene glycol hydrogel with methyl-collagen.

"Hydrostatic pressure" means pressure measured above the atmospheric pressure.

"Cyclic hydrostatic pressure" or "Cy-HP" means the application of repeated, two or multiplicity periods of applied hydrostatic pressure within a defined loading interval which creates a sine wave form of measured pressure.

"Constant hydrostatic pressure", "constant-HP" or "CHP" means the application of a non-fluctuating or non-cyclic pressure load over a period of time.

"Loading" or "loading interval" means a period of applied cyclic hydrostatic pressure load followed by a return to atmospheric pressure where no external pressure is applied.

"Resting phase" means a variable length of time wherein cells are maintained in culture at atmospheric pressure after exposure to or culturing under cyclic hydrostatic pressure.

"De novo" or "de novo formation" means the new production of cells, such as chondrocytes, fibroblasts, fibrochondrocytes, tenocytes, osteoblasts and stem cells capable of differentiation, or tissues such as cartilage connective tissue, fibrocartilage, tendon, and bone within a support structure, such as multi-layered system, scaffold or collagen matrix or formation of superficial cartilage layer.

"Superficial cartilage layer" means an outermost layer of cartilage that forms the layer of squamous-like flattened superficial zone chondrocytes covering the layer of the second sealant and overgrowing the lesion.

"Thermo-reversible" means a compound or composition changing its physical properties such as viscosity and consistency, from sol to gel, depending on the temperature. The thermo-reversible composition is typically completely in a sol (liquid) state at between about 5 and 15° C. and in a gel (solid) state at about 30° C. and above. The gel/sol state in between shows a lesser or higher degree of viscosity and depends on the temperature. When the temperature is higher than 15° C., the sol begins to change into gel and with the temperature closer to 30-37° the sol becomes more and more solidified as gel. At lower temperatures, typically lower than 15° C., the sol has more liquid consistency.

"TRGH" means thermo-reversible gelation hydrogel material in which the sol-gel transition occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature can be set at any temperature in the range from 5° C. to 70° C. by molecular design of thermo-reversible gelation polymer (TGP), a high molecular weight polymer of which less than 5 wt % is enough for hydrogel formation.

"SHTG" means space holding thermo-reversible gel.

"Sol-gel solution" means a colloidal suspension which, under certain conditions, transitions from a liquid (sol) to a solid material (gel). The "sol" is a suspension of aqueous collagen that is transitioned, by heat treatment, into a gel.

"GAG" means glycosaminoglycan.

"S-GAG" means sulfated glycosaminoglycan.

"MMP" means matrix metalloproteinase, an enzyme associated with cartilage degeneration in an injured or diseased joint.

"DMB" means dimethylene blue used for staining of chondrocytes.

"MPa" means MegaPascal. One MPa is equal to 145 psi.

"Superficial zone cartilage" means the flattened outermost layer of chondrocytes covering the extracellular matrix intermediate zone and deeper zone of mature articular cartilage in which non-dividing cells are dispersed.

"Connective tissue" means tissue that protect and support the body organs, and also tissues that hold organs together. Examples of such tissues include mesenchyme, mucous, connective, reticular, elastic, collagenous, bone, blood, or cartilage tissue such as hyaline cartilage, fibrocartilage, and elastic cartilage.

"The algorithm" means variable defined conditions, such as variable pressure or non-pressure conditions, variable perfusion rate, different medium, different cell density, different temperature, variable time, different oxygen and carbon dioxide conditions, etc., to which a cellular construct of neo-cartilage is subjected in order to convert it to a mature neo-cartilage construct.

"Adhesive strength" means a peel bond strength measurement, which can be accomplished by bonding two plastic tabs with an adhesive formulation. The tabs can be formed by cutting 1×5 cm strips from polystyrene weighing boats. To the surface of the boat are bonded (using commercial cyanoacrylate Superglue), sheets of sausage casing (collagen sheeting, available from butcher supply houses). The sausage casing is hydrated in water or physiological saline for 20 min to one hour and the adhesive is applied to a 1×1 cm area at one end of the tab; the adhesive is cured. Then, the free ends of the tab are each bent and attached to the upper and lower grips, respectively, of a tensile testing apparatus and pulled at 10 mm/min strain rate, recording the force in Newtons to peel. A constant force trace allows estimation of N/m, or force per width of the strip. A minimum force per width of 10 N/m is desired; 100N/m or higher is more desirable. Alternatively, the same tab can be bonded (a single tab) over a 1×1 cm area to tissue, either dissected or exposed tissue in a living animal, during surgery. The free end of the tab is then gripped or attached through a perforation to a hook affixed to a hand-held tensile test device (Omega DFG51-2 digital force gauge; Omega Engineering, Stamford, Conn.) and pulled upward at approximately 1 cm/sec. The maximum force required to detach the tab from the tissue is recorded. The minimum force desired in such measurements would be 0.1 N to detach the tab. Forces or 0.2 to 1 N are more desirable.

"Cohesive strength" means the force required to achieve tensile failure and is (pulling in extension); measured using a tensile test apparatus. The glue or adhesive can be cured in a "dog-bone"-shaped mold. The wide ends of the formed solid adhesive can then be affixed, using cyanoacrylate (Superglue) to plastic tabs, and gripped in the test apparatus. Force at extensional failure should be at least 0.2 MPa (2 N/cm2) but preferably 0.8 to 1 MPa or higher.

"Lap shear measurements" means a test of bonding strength, in which the sealant formulation is applied to overlapping tabs of tissue, cured, and then the force to pull the tabs apart is measured. The test reflects adhesive and cohesive bonding; strong adhesives will exhibit values of 0.5 up to 4-6 N/cm$^2$ of overlap area.

DETAILED DESCRIPTION OF THE INVENTION

This invention is based on finding that when metabolically active but non-dividing chondrocytes are processed according to the invention, they become activated and dividing. These activated and dividing chondrocytes then may be converted into neo-cartilage and upon incorporating this neo-cartilage into the support matrix and submitting said neo-cartilage/support matrix to the algorithm of the invention become a structural unit called neo-cartilage construct. Such processed neo-cartilage construct is suitable for implantation into a lesion of injured, traumatized, aged or diseased cartilage or under the top sealant or between layers of a first (bottom) and a second (top) sealant. Under these conditions the second top sealant promotes in situ formation of de novo superficial cartilage layer over the cartilage lesion.

The invention thus, in its broadest scope, concerns a method for preparation of neo-cartilage from chondrocytes harvested from a donor's tissue, a method for formation of a support matrix, a method for fabrication of a neo-cartilage construct, a method for de novo formation of a superficial cartilage layer in situ, a method for repair and restoration of damaged, injured, traumatized or aged cartilage to its full functionality, and a method for treatment of injuries or diseases caused by damaged cartilage due to the trauma, injury, disease or age.

Briefly, the invention comprises preparation of neo-cartilage from harvested autologous or heterologous chondrocytes, culturing and expansion of chondrocytes, seeding the chondrocytes within a collagenous or thermo-reversible gel support matrix and propagating said chondrocytes in two or three-dimensions. To achieve the chondrocyte propagation, the seeded support matrix is optionally subjected to the algorithm of variable conditions, such as static conditions, constant or cyclic hydrostatic pressure, temperature changes, oxygen and/or carbon dioxide level changes and changes in perfusion flow rate of the culture medium in the presence of various supplements, such as, growth factors, donor's serum, ascorbic acid, ITS, etc. The chondrocyte-seeded support matrix treated as above becomes a neo-cartilage construct (neo-cartilage) suitable for implanting into a joint cartilage lesion.

The neo-cartilage construct is implanted into the lesion under a top sealant, or into a cavity formed by two layers of adhesive sealants. The first layer of the sealant is deposited at and covers the bottom of the lesion and its function is to protect the integrity of said lesion from cell migration and from effects of various blood and tissue metabolites and also to form a bottom of the cavity into which the neo-cartilage construct is deposited.

In one embodiment, after the neo-cartilage construct is emplaced into the lesion cavity, the second adhesive layer is deposited on the top of the neo-cartilage construct and within several months results in formation of the superficial cartilage layer completely sealing the lesion.

In the alternative embodiment, two adhesive layers may be deposited concurrently with or before the construct is implanted into the cavity between them. In such an instance, in the interim, said cavity may be filed with a space holding thermo-reversible gel (SHTG). Both sealant layers and the construct or space holding gel are left within the lesion cavity for a certain predetermined period of time, typically from one week to several months, or in case of the space holding gel, until the neo-cartilage construct is prepared ex vivo and ready to be implanted. The second layer deposited on the top and over the lesion promotes formation of a superficial cartilage layer which covers the lesion on the outside and eventually overgrows the lesion completely thereby resulting in complete or almost complete sealing of the lesion and of the neo-cartilage construct deposited within said lesion leading to incorporation of neo-cartilage into a native cartilage and resulting in healing of the injured or damaged cartilage. In alternative, the thermo-reversible gel may serve as an initiator for promotion of formation of the superficial cartilage layer.

Both the support matrix of the neo-cartilage construct or the space holding thermo-reversible gel deposited into the lesion are materials which are biodegradable and permit and promote formation of the superficial cartilage layer and integration of the chondrocytes from the neo-cartilage construct into the native cartilage within the lesion cavity. Such integration begins within several weeks or months following the implanting and may continue for several months and involves a growth and maturing of neo-cartilage into normal cartilage integrated into the healthy cartilage. The top sealant layer promotes an overgrowth of the lesion with the superficial cartilage layer typically in about two-three months when the sealant is itself degraded.

In the alternative embodiment, the lesion cavity is filled with a space-holding gel until the outer superficial cartilage layer is formed at which time the neo-cartilage construct comprising ex vivo propagated chondrocytes suspended in a thermo-reversible sol is introduced at a temperature between 5° and 15° C. After it is introduced into the lesion as a liquid sol, the introduced thermo-reversible sol-gel is converted into a solid gel at body temperatures of 37° C. or at the same or similar temperature as the temperature of the synovial cavity. The neo-cartilage construct introduced into the lesion is integrated into the native cartilage surrounding the cavity and is completely covered with the superficial cartilage layer.

In the alternative, the neo-cartilage construct is deposited into a lesion of injured, traumatized, aged or diseased cartilage over the first (bottom) sealant layer and the thermo-reversible gel of the neo-cartilage construct promotes in situ formation of the superficial membrane without a need to add the second sealant.

The method for treatment of injured, traumatized, diseased or aged cartilage comprises treating the injured, traumatized, diseased or aged cartilage with an implanted neo-cartilage construct prepared by methods described above and/or by any combination of steps or components as described.

I. Preparation of Neo-Cartilage Constructs

Preparation of neo-cartilage constructs for implanting into the cartilage lesion involves harvesting and culturing chondrocytes, seeding them in the support matrix and preparation thereof, and propagating the chondrocytes either ex vivo, in vitro, or in vivo.

A. Cartilage and Neo-Cartilage

Cartilage is a connective tissue covering joints and bones. Neo-cartilage is immature cartilage which eventually, upon deposition into the lesion according to this invention, is integrated into and acquires properties of mature cartilage. Differences between the two types of cartilage is in their maturity. Cartilage is a mature tissue comprising metabolically active but non-dividing chondrocytes; neo-cartilage is an immature cartilage comprising metabolically and genetically activated chondrocytes which are able to divide and multiply. This invention utilizes properties of neo-cartilage in achieving repair and restoration of damaged cartilage into the full functionality of the healthy cartilage by enabling the neo-cartilage to be integrated into the mature cartilage surrounding the lesion and in this way repair the defect.

a) Cartilage

Cartilage is a connective tissue characterized by its poor vascularity and a firm consistency. Cartilage consist of mature non-dividing chondrocytes (cells), collagen (interstitial matrix of fibers) and a ground proteoglycan substance (glycoaminoglycans or mucopolysaccharides). Later two are cumulatively known as extracellular matrix.

There are three kinds of cartilage, namely hyaline cartilage, elastic cartilage and fibrocartilage. Hyaline cartilage found primarily in joints has a frosted glass appearance with interstitial substance containing fine type II collagen fibers obscured by proteoglycan. Elastic cartilage is a cartilage in which, in addition to the collagen fibers and proteoglycan, the cells are surrounded by a capsular matrix surrounded by an interstitial matrix containing elastic fiber network. The elastic cartilage is found, for example, in the central portion of the epiglottis. Fibrocartilage contains Type I collagen fibers and is typically found in transitional tissues between tendons, ligaments or bones.

The articular cartilage of the joints, such as the knee cartilage, is the hyaline cartilage which consists of approximately 5% of chondrocytes (total volume) seeded in approximately 95% extracellular matrix (total volume). The extracellular matrix contains a variety of macromolecules, including collagen and proteoglycan. The structure of the hyaline cartilage matrix allows it to reasonably well absorb shock and withstand shearing and compression forces. Normal hyaline cartilage has also an extremely low coefficient of friction at the articular surface.

Healthy hyaline cartilage has a contiguous consistency without any lesions, tears, cracks, ruptures, holes or shredded surface. Due to trauma, injury, disease such as osteoarthritis, or aging, however, the contiguous surface of the cartilage is disturbed and the cartilage surface shows cracks, tears, ruptures, holes or shredded surface resulting in cartilage lesions. Partly because hyaline cartilage is avascular, the spontaneous healing of large defects is not believed to occur in humans and other mammals and the articular cartilage has thus only a limited, if any, capacity for repair.

A variety of surgical procedures have been developed and used in attempts to repair damaged cartilage. These procedures are performed with the intent of allowing bone marrow cells to infiltrate the defect and promote its healing. Generally, these procedures are only partly successful. More often than not, these procedures result in formation of a fibrous cartilage tissue (fibrocartilage) which does fill and repair the cartilage lesion but, because it is qualitatively different being made of Type I collagen fibers, it is less durable and less resilient than the normal articular (hyaline) cartilage and thus has only a limited ability to withstand shock and shearing forces than does healthy hyaline cartilage. Since all diarthroid joints, particularly knees joints, are constantly subjected to relatively large loads and shearing forces, replacement of the healthy hyaline cartilage with fibrocartilage does not result in complete tissue repair and functional recovery.

b) Neo-Cartilage

Neo-cartilage is an immature hyaline cartilage where the ratio of extracellular matrix to chondrocytes is lower than in mature hyaline cartilage. Mature hyaline cartilage has the ratio of the extracellular matrix to chondrocytes approximately 95:5. The neo-cartilage has a lower ratio of the extracellular matrix to chondrocytes than mature cartilage and thus comprises more than 5% of chondrocytes.

In the process of development of this invention, it was discovered that under the conditions described below, the older inactive chondrocytes could be activated from static non-dividing stage to an active stage where they divide, multiply, promote growth of the extracellular matrix and develop into new cartilage (neo-cartilage). The neo-cartilage thus contains chondrocytes which were rejuvenated and are surrounded by a newly synthesized extracellular-matrix macromolecules. A process for activation was found to require certain period of time, typically from about 1 week to about 3 months and it is thus preferred that the neo-cartilage be prepared ex vivo where nutrients needs and mechanical loading are well defined.

B. Preparation of Neo-Cartilage

Neo-cartilage prepared according to the current invention is grown ex vivo from chondrocytes isolated from the mammalian donor's source. In the alternative, neo-cartilage may also be grown in situ or in vivo under conditions described below.

Typical donor sources of mammalian chondrocytes are swine or humans. Neo-cartilage of the invention for human use is preferably grown from autologous chondrocytes obtained from the patient during arthroscopy. While it is preferred that for human use chondrocytes are autologous, it is to be understood that chondrocytes obtained from other mammalian sources are equally suitable for preparation of neo-cartilage for treatment of damaged, diseased or aged cartilage. The use of both autologous and heterologous chondrocytes is intended to be within the scope of the invention.

a) Isolation of Chondrocytes

Specific procedures used for isolation of mammalian chondrocytes generally using swine cartilage as an example are described in Example 1. The isolation of human chondrocytes and preparation of autologous human neo-cartilage is according to procedures described in Example 2.

Briefly, the donor cartilage is obtained either by arthroscopic biopsy from the human donor or from a joint or bone, such as, for example, the femur of the slaughtered animal and processed according to Example 1 or 2. The cartilage is preferably digested by collagenase, a strong protease, most preferably Type I collagenase, in a solution containing preferably about 0.15% of collagenase. The digestion is run for several hours to several days, preferably for about 18 hours.

In alternative, the extracellular matter can be digested with proteases or sugar lyases including but not limited to heparitinase, heparinase, chondroitinase ABC, chondroitinase B and chondroitinase AC. The lyases are added in admixture with collagenase or in a sequential enzyme digestion steps. These lyases promote further isolation of the chondrocytes from the extracellular matrix (ECM) including disruption the glycosaminoglycans of the pericellular environment such that the chondrocytes do not receive inhibitory signals that prevent them from dividing or producing healthy new extracellular matrix. This finding is especially important for osteoarthritic chondrocytes which have very slow division rates and reduced ability to produce extracellular matrix.

This is especially important for osteoarthritic chondrocytes which have very slow division rates and reduced ability to produce ECM. U.S. Pat. No. 5,916,557 shows that application of chondroitinase ABC to chondrocytes in vitro resulted couterintuitively in the promotion of new cartilage production.

The ability to free the chondrocytes from all extra- and pericellular inhibitory material and thereby to promote cell expansion and differentiation is especially important in autologous osteoarthritic tissue where the growth is otherwise slow because these chondrocytes have reduced ability to produce ECM where neo-cartilage formation in the TESS processor under pressure is greatly improved by this early step of the process. Furthermore, this method of stimulating chondrocyte growth and differentiation is relatively benign compared to the application of growth factors or other chemical stimuli at a later stage of the formation of neo-cartilage, since the cells are washed free of the enzymes before culturing.

b) Expansion of Chondrocytes

The isolated chondrocytes are then expanded by any method suitable for such purposes such as, for example, by incubation in a suitable growth medium, for a period of several days, typically from about 3 to about 30 days, preferably for 14 days, at about 37° C. Any kind of culture or incubation apparatus or chamber may be used for expanding chondrocytes. The expansion of the cells is preferably associated with the removal of dead chondrocytes, residual native extracellular matrix and other cellular debris before the chondrocytes are selected for culturing and multiplying. Selected chondrocytes are collected and isolated using trypsinization process or any other suitable method.

Expanded chondrocytes are then suspended in a suitable solution and seeded into a support matrix to form a seeded matrix. The seeded matrix is typically processed in a tissue processor.

c) Suspension and Seeding of Chondrocytes in the Support Matrix

Following the expansion, chondrocytes are suspended in any suitable solution, preferably collagen containing solution. For the purposes of this invention such solution is typically a gel, preferably sol-gel transitional solution which changes the state of the solution from liquid sol to solid gel above room temperature. The most preferred such solution is the thermo-reversible gelation hydrogel or a thermo-reversible polymer gel. The thermo-reversible property is important both for immobilization of the chondrocytes within the support matrix and for implanting of the neo-cartilage construct within the cartilage lesion.

One characteristic of the sol-gel is its ability to be cured or transitioned from a liquid into a solid form. This property may be advantageously used for solidifying the suspension of chondrocytes withing the support matrix for delivery, storing or preservation purposes. Additionally, these properties of sol-gel also permit its use as a support matrix by changing its sol-gel transition by increasing or decreasing temperature, as described in greater detail below for thermo-reversible gelation hydrogel, or exposing the sol-gel to various chemical or physical conditions or ultraviolet radiation.

In one embodiment the expanded chondrocytes are suspended in a collagenous sol-gel solution before incorporation (seeding) into the support matrix. The sol-gel viscosity permits easy mixing of chondrocytes avoiding need to use shear forces. One example of the suitable sol-gel solution is the solution substantially composed of Type I collagen, commercially available under trade name VITROGEN® from Cohesion Corporation, Palo Alto, Calif. VITROGEN is a purified pepsin-solubilized bovine collagen dissolved in 0.012N HCl. Sterile collagen for tissue culture may be additionally obtained from other sources, such as, for example, Collaborative Biomedical, Bedford, Mass., and Gattefosse, S A, St Priest, France.

When using a VITROGEN solution, the cell density is approximately $5-10 \times 10^6$ cells/mL. However, both the density of the cells, the volume for their seeding and strength of the solution are variables within the algorithm, and the higher or lower number of chondrocytes may be suspended in a larger or lower volume of the suspension solution, depending on the size of the support matrix and the size of the cartilage lesion.

Seeding of the suspended chondrocytes into the support matrix is by any means which permit even distribution of the chondrocytes within said support matrix. Seeding may be achieved by bringing the suspension and the support matrix into close contact and seeding the cells by wicking or suction of the suspension into the matrix by capillary action, by inserting the support matrix into the suspension, by using suction, positive or negative pressure, injection or any other means which will result in even distribution of the chondrocytes within said support matrix.

In alternative embodiment, the chondrocytes are suspended in the thermo-reversible gelation hydrogel or gel polymer at temperature between 5 and 15° C. At that temperature, the hydrogel is at a liquid sol stage and easily permits the chondrocytes to be suspended in the sol. Once the chondrocytes are evenly distributed within the sol, the sol is subjected to higher temperature of about 30-37° C. at which temperature, the liquid sol solidifies into solid gel having evenly distributed chondrocytes within. The gelling time is from about several minutes to several hours, typically about 1 hour. In such an instance, the solidified gel may itself become and be used as a support matrix or the suspension in sol state may be loaded into a separate support matrix, such as a sponge or honeycomb support matrix.

Other means of generating suspending gels, not necessarily thermo-reversible, are also available and suitable for use. Polyethylene glycol (PEG) derivatives, in which one PEG chain contains vinyl sulfone or acrylate end groups, and the other PEG chain contains free thiol groups will covalently bond to form thio-ether linkages. If one or both partner PEG molecules are branched (three- or four-armed), the coupling results in a network, or gel. If the molecular weight of the PEG chains is several thousand Daltons (500 to 10,000 Daltons along any linear chain segment), the network will be open, swellable by water, and compatible with living cells. The coupling reaction can be accomplished by preparing 5 to 20% (w/v) solutions of each PEG separately in aqueous buffers or cell culture media. Chondrocytes can be added to the thiol-PEG solution. Just prior to incorporation into the support matrix, the cells plus thiol PEG and the acrylate or vinyl sulfone PEG are mixed and infused into the matrix. Gelation will begin spontaneously in 1 to 5 minutes; the rate of gelation can be modulated somewhat by the concentration of PEG reagent and by pH. The rate of coupling is faster at pH 7.8 than at pH 6.9. Such gels are not degradable unless additional ester or labile linkages are incorporated into the chain. Such PEG reagents may be purchased from Shearwater Polymers, Huntsville, Ala., USA; or from SunBio, Korea.

In a second alternative, alginate solutions can be gelled in the presence of calcium ions. This reaction has been employed for many years to suspend cells in gels or microcapsules. Cells can be mixed with a 1-2% (w/v) solution of alginate in culture media devoid of calcium or other divalent ions, and infused into the support matrix. The matrix can then be immersed in a solution containing calcium chloride, which will diffuse into the matrix and gel the alginate, trapping and supporting the cells. Analogous reactions can be accomplished with other polymers which bear negatively charged carboxyl groups, such as hyaluronic acid. Viscous solutions of hyaluronic acid can be used to suspend cells and gelled by diffusion of ferric ions.

Suspension loaded into the support matrix or gelled into the solid support is processed using the algorithm of the invention. Such processing is performed in a processing apparatus, such as a TESS processor.

C. Preparation of Support Matrix

The support matrix for seeding expanded chondrocytes provides a structural support for growth and two or three-dimensional propagation of chondrocytes. Generally, the support matrix is biologically biocompatible, hydrophilic and has preferably a neutral charge.

Typically, the support matrix is a two or three-dimensional structural composition, or a composition able to be converted into such structure, containing a plurality of pores dividing the space into a fluidically connected interstitial network. In some embodiments the support matrix is a sponge-like structure or honeycomb-like lattice.

In general, any polymeric material can serve as the support matrix, provided it is biocompatible with tissue and possesses the required geometry. Polymers, natural or synthetic, which can be induced to undergo formation of fibers or coacervates, can then be freeze-dried as aqueous dispersions to form sponges. Typically, such sponges must be stabilized by crosslinking, such as, for example, ionizing radiation. Practical example includes preparation of freeze-dried sponges of poly-hydroxyethyl-methacrylate (pHEMA), optionally having additional molecules, such as gelatin, entrapped within advantageously. Such types of sponges can advantageously function as support matrices for the present invention. Incorporation of agarose, hyaluronic acid, or other bio-active polymers can be used to modulate cellular responses. A wide range of polymers may be suitable for the fabrication of support matrix sponges, including agarose, hyaluronic acid, alginic acid, dextrans, polyHEMA, and poly-vinyl alcohol above or in combination.

Typically, the support matrix is prepared from a collagenous gel or gel solution containing Type I collagen, Type II collagen, Type IV collagen, gelatin, agarose, hyaluronin, cell-contracted collagens containing proteoglycans, glycosaminoglycans or glycoproteins, fibronectin, laminin, bioactive peptide growth factors, cytokines, elastin, fibrin, synthetic polymeric fibers made of poly-acids such as polylactic, polyglycotic or polyamino acids, polycaprolactones, polyamino acids, polypeptide gel, copolymers thereof and combinations thereof. Preferably, the support matrix is a gel solution, most preferably containing aqueous Type I collagen or a polymeric, preferably thermo-reversible, gel matrix.

The gel or gel solution used for preparation of the support matrix is typically washed with water and subsequently freeze-dried or lyophilized to yield a sponge like matrix able to incorporate or wick the chondrocytes suspension withing the matrix. The cellular support matrix of the current invention acts like a sponge when infiltrated with the chondrocyte suspension wherein the cells are evenly distributed.

One important aspect of the support matrix is the pore size of the support matrix. Support matrices having different pore sizes permit faster or slower infiltration of the chondrocytes into said matrix, faster or slower growth and propagation of the cells and, ultimately, the higher or lower density of the cells in the neo-cartilage construct. Such pore size may be adjusted by varying the pH of the gel solution, collagen concentration, lyophilization conditions, etc. Typically, the pore size of the support matrix is from about 50 to about 500µ, preferably the pore size is between 100 and 300µ and most preferably about 200µ.

The support matrix may be prepared according to procedures described in Example 3, or by any other procedure, such as, for example, procedures described in the U.S. Pat. Nos. 6,022,744; 5,206,028; 5,656,492; 4,522,753 and 6,080,194 herein incorporated by reference.

One preferred type of support matrix is Type-I collagen support matrix fabricated into a sponge, commercially available from Koken Company, Ltd., Tokyo, Japan, under the trade name Honeycomb Sponge.

Figure 1B:
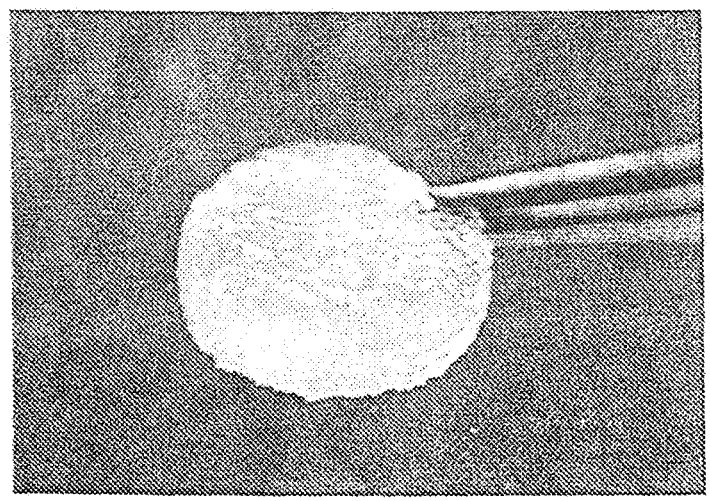
FIG. 1B is a micrograph of the actual neo-cartilage construct held in the forceps having 4 mm in diameter and thickness of 1.5 mm. Seeding density of the construct is 300,000 chondrocytes per 25 μl of collagen solution (12,000,000 cells/ml).

An exemplary neo-cartilage support matrix made of collagen and embedded with chondrocytes is seen in FIG. 1, wherein FIG. 1A is a schematic drawing of the sponge made of sol/gel showing the distribution of chondrocytes within the collagen sponge. FIG. 1B shows a microphotograph of the actual neo-cartilage construct (Neo-Cart™) having 4 mm in diameter and thickness of 1.5 mm. The seeding density of this construct is 300,000-375,000 chondrocytes per 25 µl of collagen solution corresponding to about 12-15 millions cells/mL. The cell density range for seeding is preferably from about 3 to about 60 millions/mL.

a) Honeycomb Cellular Support Matrix

In one embodiment of the invention, the support matrix is a honeycomb-like lattice matrix providing a cellular support for activated chondrocytes, herein described as neo-cartilage.

The honeycomb-like matrix supports a growth platform for the neo-cartilage and permits three-dimensional propagation of the neo-cartilage.

The honeycomb-like matrix is fabricated from a polymerous compound, such as collagen, gelatin, Type I collagen, Type II collagen or any other polymer having a desirable properties. In the preferred embodiment, the honeycomb-like matrix is prepared from a solution comprising Type I collagen.

The pores of the honeycomb-like matrix are evenly distributed within said matrix to form a sponge-like structure able to taking in and evenly distributing the neo-cartilage suspended in a viscous solution.

b) Sol-Gel Cellular Support Matrix

In another embodiment, the support matrix is fabricated from sol-gel materials wherein said sol-gel materials can be converted from sol to gel and vice versa by changing temperature. For these materials the sol-gel transition occurs on the opposite temperature cycle of agar and gelatin gels. Thus, in these materials the sol is converted to a solid gel at a higher temperature. Sol-gel material is a material which is a viscous sol at temperatures of below 15° and a solid gel at temperatures around and above 37°. Typically, these materials change their form from sol to gel by transition at temperatures between about 15° and 37° and are in transitional state at temperatures between 15° C. and 37°. The most preferred materials are Type I collagen containing gels and a thermo-reversible gelation hydrogel (TRGH) which has a rapid gelation point.

In one embodiment, the sol-gel material is substantially composed of Type I collagen and, in the form of 99.9% pure pepsin-solubilized bovine dermal collagen dissolved in 0.012N HCl, is commercially available under the tradename VITROGEN® from Cohesion Corporation, Palo Alto, Calif. One important characteristic of this sol-gel is its ability to be cured by transition into a solid gel form wherein said gel cannot be mixed or poured or otherwise disturbed thereby forming a solid structure containing immobilized chondrocytes.

Type I collagen sol-gel is generally suitable for suspending the chondrocytes and for seeding them into a separately prepared support matrix in the sol form and gel the sol into the solid gel by heating the support matrix to a proper temperature, usually around 30-37° and, in this form, processing the embedded support matrix. This type of sol-gel can also be used as a support matrix for purposes of processing the gel containing chondrocytes in the processor of the invention into a neo-cartilage construct.

In another embodiment, the sol-gel is thermo-reversible gelation hydrogel (TRGH). Sol-gel thermo-reversible material for preparation of sol-gel support matrix is a material which is a viscous sol at temperatures of below 15-30° C. and solid gel at temperatures above 30-37° C. The primary characteristic of the thermo-reversible gelation hydrogel (TRGH) is that it gels at body temperature and sols at lower than 15-30° C. temperature, that upon its degradation within the body it does not leave biologically deleterious material and that it does not absorb water at gel temperatures. TRGH has a very quick sol-gel transformation which requires no cure time and occurs simply as a function of temperature without hysteresis. The sol-gel transition temperature can be set at any temperature in the range from 5° C. to 70° C. by the molecular design of the thermo-reversible gelation polymer (TGP), a high molecular weight polymer of which less than 5 wt % is enough for hydrogel formation.

The typical TRGH is generally made of blocks of high molecular weight polymer comprising numerous hydrophobic domains cross-linked with hydrophilic polymer blocks. TRGH has low osmotic pressure and is very stable as it is not dissolved in water when the temperature is maintained above the sol-gel transition temperature. Hydrophilic polymer blocks in the hydrogel prevent macroscopic phase separation and separation of water from hydrogel during gelation. These properties make it especially suitable for safe storing and extended shelf-life.

The thermo-reversible gelation hydrogel (TRGH), particularly a space-holding thermo-reversible gel (SHTG), should be a compressively strong and stable at 37° C. and below till about 32° C., that is to about temperature of the synovial capsule of the joint which is typically below 37° C., but should easily solubilize below 30-31° C. to be able to be conveniently removed from the cavity as the sol. The compressive strength of the SHTG or TRGH must be able to resist compression by the normal activity of the joint.

In this regard, the thermo-reversible hydrogel is an aqueous solution of thermo-reversible gelation polymer (TGP) which turns into hydrogel upon heating and liquefies upon cooling. TGP is a block copolymer composed of temperature responsive polymer (TRP) block, such as poly(N-isopropylacrylamide) or polypropylene oxide and of hydrophilic polymer blocks such as polyethylene oxide.

Thermally reversible hydrogels consisting of co-polymers of polyethylene oxide and polypropylene oxide are available from BASF Wyandotte Chemical Corporation under the trade name of Pluronics.

In general, thermo-reversibility is due to the presence of hydrophobic and hydrophilic groups on the same polymer chain, such as in the case of collagen and copolymers of polyethylene oxide and polypropylene oxide. When the polymer solution is warmed, hydrophobic interactions cause chain association and gelation; when the polymer solution is cooled, the hydrophobic interaction disappears and the polymer chains are dis-associated, leading to dissolution of the gel. Any suitably biocompatible polymer, natural or synthetic, with such characteristics will exhibit the same reversible gelling behavior.

This type of thermo-reversible gelation hydrogel is particularly preferred for preparation of neo-cartilage constructs for implantation of the construct into the lesion. In such an instance, the harvested chondrocytes are suspended in the TRGH sol, then warmed to about 37° C. into the solid gel which thus itself becomes a seeded support matrix, then submitting said seeded matrix to the processing in the tissue processor using the algorithm of the invention, including resting period as described below, thereby resulting in a formation of the neo-cartilage construct, then submitting said construct to cooling to change its form into a sol and in this form injecting the neo-cartilage into the lesion wherein upon warming to body temperature the sol is immediately converted into the gel containing neo-cartilage. In time, the delivered neo-cartilage is integrated into the existing cartilage and the TRGH is subsequently degraded leaving no undesirable debris behind.

D. Processing Neo-Cartilage and Tissue Processors

In order to promote three-dimensional growth and propagation of chondrocytes and/or neo-cartilage, it is advantageous and/or necessary in certain instances to facilitates such growth and propagation by changing conditions of their growth. Such facilitation may be initiated either ex vivo, in vitro or in vivo.

This process is, in the current invention, achieved by subjecting either the suspended expanded chondrocytes or the support matrix incorporated with suspended chondrocytes to certain protocol (the algorithm) of conditions which were found to promote such propagation. Such conditions are, for example, application of constant or cyclic hydrostatic pressure, resting periods at static pressure, recirculation and changing flow rate of media, regulation of oxygen or carbon dioxide concentrations, cell density, control pH, availability of nutrients and co-factors, etc. Typically, this process is performed in the apparatus, preferably in the TESS™ tissue processor, permitting changing of the conditions, as stated above.

a) Neo-Cartilage Tissue Processor

The general design of the tissue processor is the apparatus for culturing chondrocytes comprising a culture unit having a culture chamber containing culture medium and a supply unit for the continuous and intermittent delivery of the culture medium, a pressure generator for applying atmospheric or constant or cyclic hydrostatic pressure above the atmospheric pressure to chondrocytes in the tissue chamber, said generator having means for changing the pressure, timing, or applying the atmospheric, constant or cyclic hydrostatic pressure at predetermined periods and, optionally, a means capable of delivering and/or absorbing gases such as nitrogen, carbon dioxide and oxygen. Additionally, the processor typically comprises a hermetically sealed space including a heating, cooling and humidifying means.

Figure 2A:
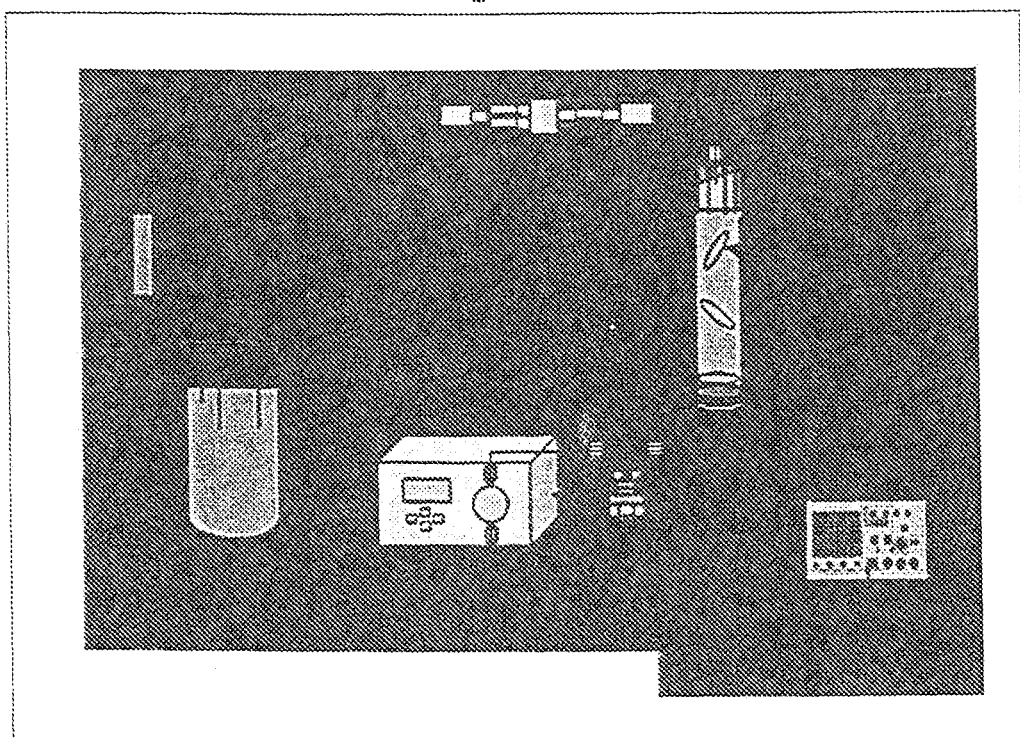
FIG. 2A shows a diagram of hydrostatic pressure culture system.
Figure 2B:
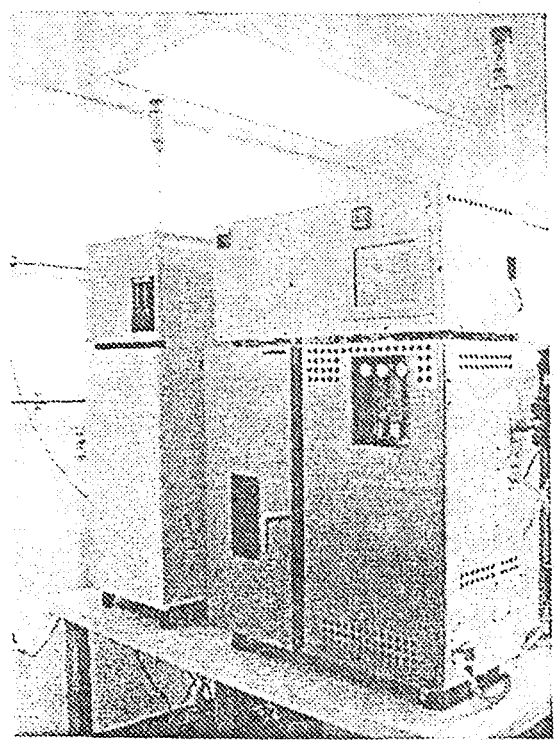
FIG. 2B shows a TESS culture processor unit.

An exemplary scheme of the tissue processor suitable for applying of static or hydrostatic pressure, changing flow rate of the medium and regulating gas concentration delivered to the embedded support system suitable for purposes of this invention is seen in FIG. 2A. The tissue processor, seen in FIG. 2B, known as Tissue Engineering Support System (TESS) is described in the U.S. Pat. No. 6,432,713 issued on Aug. 13, 2002, and also in the U.S. application Ser. No. 09/895,162, both hereby incorporated by reference.

b) Biochemical and Histological Testing of Neo-Cartilage Constructs

The neo-cartilage constructs are tested for their metabolic activity, genetic activation and histological appearance.

Typically, the constructs are harvested at days 6 and 18. For histological evaluation of the immature and mature cartilage matrix, 4% paraformaldehyde-fixed paraffin sections are stained with Safranin-O and Type II collagen antibody. For biochemical analysis, neo-cartilage constructs are digested in papain at 60° C. for 18 hours and DNA is measured using, for example, Hoechst 33258 dye method as described in *Anal. Biochem.*, 174:168-176 (1988). The production of glycoaminoglycan (GAG) or sulfated-glycosaminoglycan (S-GAG) indicating a metabolic activity of the chondrocyte culture is tested using, for example, modified dimethylene blue (DMB) microassay according to *Connective Tissue Research*, 9:247-248 (1982).

c) Conditions for Propagation of Chondrocytes, Preparation of Neo-Cartilage and Neo-Cartilage Constructs Neo-cartilage construct, as used herein, means a matrix embedded with chondrocytes and processed according to the invention.

Neo-cartilage constructs may be produced as 3-dimensional patches comprising neo-cartilage having an approximate size of the lesion into which they are deposited or they may be produced as 3-dimensional sheet for use in repairs of extensive cartilage injuries. Their size and shape is determined by the shape and size of the support matrix. Their functionality is determined by the conditions (the algorithm) under which they were processed.

Conditions for three-dimensional propagation of chondrocytes in the support matrix into neo-cartilage construct are variable and are adjusted according to the intended use and/or function of the neo-cartilage and depend on the type of used thermo-reversible hydrogel and on the density of the seeded cells. Thus for production of small neo-cartilage constructs, the conditions will be different from those needed for production of large constructs or for production of extensive neo-cartilage sheets for partial or total replacement of extensively damaged or diseased, for example osteoarthritic, cartilage.

i) Processing Neo-Cartilage Under Variable Flow

One aspect of this invention is the discovery that if the support matrix seeded with chondrocytes is perfused under varying medium flow rates, the cell proliferation, measured by increased accumulation of the extracellular matrix, can be advantageously increased or decreased. Generally, the lower medium flow rate results in the higher extracellular matrix accumulation.

Perfusion is an important variable condition for culturing chondrocytes incorporated into support matrices. Using a faster perfusion flow rate may slow down extracellular matrix accumulation affecting growth and propagation of chondrocytes, as measured by production of sulfated glycosaminoglycan (S-GAG). A slower perfusion rate, on the other hand, results in higher production of S-GAG. These results are important for controlling the neo-cartilage growth and for, for example, storage, preservation, transport and shelf-life of neo-cartilage constructs.

The perfusion flow rate suitable for purposes of this invention is from about 1 to about 500 µl/min, preferably from about of 5 to about 50 µl/min. At the medium perfusion rate 5 µl/min the accumulation of extracellular matrix is significantly ($p<0.05$) increased compared to accumulation of extracellular matrix observed following perfusion at rate 5 µl/min. The optimum flow rate depends upon the total number of cells in the culture chamber.

ii) Processing Neo-Cartilage Under Different Types of Pressure

Subjecting the seeded support matrix to hydrostatic pressure, in conjunction with a decreased perfusion flow, is an integral part of the culture processing system according to this invention. Different types of hydrostatic pressure have a significant effect on glycosaminoglycan production and thus on extracellular matrix accumulation compared to the effect of atmospheric pressure alone. The hydrostatic pressure, particularly cyclic hydrostatic pressure applied according to this invention has been found to stimulate chondrocyte proliferation and metabolism which contributes to extracellular matrix accumulation.

Hydrostatic pressure suitable for processing chondrocytes embedded within the support matrix is either a constant or cyclic hydrostatic pressure, such pressure being the pressure above the atmospheric pressure. The cyclic hydrostatic pressure suitable for use in processing of the seeded support matrix is from about 0.01 to about 10.0 MPa, preferably from about 0.5 to about 5.0 MPa and most preferably at about 3.0 MPa at 0.01 Hz to about 2.0 Hz, preferably at about 0.5 Hz, applied for about 1 hour to about 30 days, preferably about 7 to about 14 days, with or without resting period. Typically, the period of hydrostatic pressure is followed by the resting period, typically from about 1 day to about 60 days, preferably for about 7 to about 28 days, most preferably for about 12 to about 18 days.

Studies performed in support of this invention indicate that cell viability is not affected by the hydrostatic pressure and is maintained with chondrocytes distributed uniformly within the support matrix. Following the treatment with hydrostatic pressure, accumulations of both DNA and S-GAG are significantly increased compared to cultures not experiencing applied load, indicating that chondrocyte activation and metabolic and genetic activity can be controlled by the culture environment.

iii) Processing Neo-Cartilage Under Reduced Oxygen Concentration

Another variable in the processing of seeded support matrices is the concentration of oxygen, carbon dioxide and nitrogen.

The chondrocytes-embedded support matrix described above may be further cultured under reduced $O_2$ concentration (i.e. less than 20% saturation) during formation of neo-cartilage in the TESS processor. The reduced oxygen concentration of cartilage has been observed in vivo, and such reduction may be due to its normal lack of vascularization which produces a lower oxygen partial pressure, as compared to the adjacent tissues. In this set of studies, chondrocytes seeded in support matrix or neo-cartilage were cultured under oxygen concentration between about 0% and about 20% saturation or under dioxide concentration about 5%.

E) Determination of Conditions for Optimization of The Algorithm

The ultimate aim of this invention was to find and confirm conditions (the algorithm) for preparation of neo-cartilage constructs for implantation into cartilage lesions, which in conjunction with deposition of one or two sealant layers, would lead to healing of the damaged, injured, diseased or aged cartilage by a) growth of superficial cartilage layer completely overgrowing and covering the lesion and protecting implanted neo-cartilage construct; b) integration of neo-cartilage implanted into the lesion as the neo-cartilage construct; and c) subsequent degradation of the construct and sealant materials.

The underlying studies, described below, show that a properly designed and optimized culture conditions utilizing hydrostatic pressure with medium perfusion followed by constant culture result in fabrication of neo-cartilage constructs which are integrated into the native cartilage when implanted under the one layer or in between two layers of sealants according to the invention.

General design for a method for preparation of neo-cartilage constructs comprises steps:
 a) isolation of chondrocytes from a donor tissue;
 b) expanding the chondrocytes for about 3-28 days;
 c) seeding chondrocytes in a thermo-reversible or collagen gel or collagen sponge support matrix;
 d) subjecting the seeded gel or sponge to a static, constant or cyclic hydrostatic pressure above atmospheric pressure (about 0.5-3.0 MPa at 0.5 Hz) with medium perfusion rate of 5 µl/min for several (5-10) days; and
 e) subjecting the seeded gel or sponge to resting period for ten to fourteen days at constant (atmospheric) pressure.

Neo-cartilage constructs obtained by the above-outlined conditions and method show that the combined algorithm of hydrostatic pressure and static pressure has advantage over conventional culture methods by resulting in higher cell proliferation and extracellular matrix accumulation. Use of thermo-reversible or collagen gel or collagen sponge support matrix maintains uniform cell distribution within the support matrix and also provides support for newly synthesized extracellular matrix. Obtained 3-dimensional neo-cartilage construct is easy to handle and manipulate and can be easily and safely implanted in a surgical setting.

Combination of a period of cyclic hydrostatic pressure under low medium perfusion rate followed up with a period of static culture (resting period) results in increased cell proliferation, increased production of Type II collagen, increased DNA content and increased S-GAG accumulation.

Increased cell proliferation shows that the harvested inactive non-dividing chondrocytes have been activated into neo-cartilage containing active, dividing and multiplying chondrocytes. Increased level of DNA shows genetic activation of inactive chondrocytes. Increased production of Type II collagen and S-GAG shows that production of the extracellular matrix has been activated using the algorithm described above.

Although the optimized algorithm described above is preferred, it is to be understood that this algorithm may be advantageously changed using variations of ranges of cyclic hydrostatic pressure, flow rate, duration of the pressure and resting period as disclosed above in detail description of each condition. All variations of all conditions and combinations thereof are intended to be within the scope of this invention.

F. Supporting Experimental Studies

In order to test effects of different conditions on the propagation of chondrocytes within the support matrix for fabrication of the neo-cartilage construct, studies combining conditions described above for process optimization were performed during development of this invention. Results are shown in FIGS. 3-9 and in Tables 1-3.

For all following studies, the experimental design was as follows with changes in studies conditions.

Cartilage was harvested under sterile conditions from the trachea of the swine hind limbs, minced and digested, as described in Example 7. Chondrocytes were expanded for 5 days at 37° C. and suspended in VITROGEN® (300,000/30 µl). The suspension was absorbed into a support matrix, usually a collagen sponge (4 mm in diameter and 2 mm in thickness) as seen in FIG. 1, commercially available from Koken Co., Tokyo, Japan. The sponges seeded with chondrocytes were pre-incubated for 1 hour at 37° C. to gel the collagen, followed by incubation in culture medium at 37° C., 5% $CO_2$ and cultured in the Tissue Engineering Support System (TESS™) processor seen in FIG. 2.

a) Evaluation of Effect of Hydrostatic Pressure

To evaluate the effect of the pressure and/or medium perfusion rate, the cell seeded sponges were subjected to medium perfusion at 5 µl/min (0.005 mL/min) or 50 mL/min (0.05 mL/min) under the cyclic (Cy-HP) or constant hydrostatic pressure (constant-HP) of 0.5 MPa at 0.5 Hz for 6 days in the TESS processor. Resting period under atmospheric pressure followed for 12 days. Some seeded sponges served as controls. These were incubated under the atmospheric pressure and without perfusion at 37° C. for a total of 18 days in culture. Sponges harvested 24 hours after seeding with cells (day 0) served as an initial control. More detailed conditions are to be found in Examples and in the following text.

At the end of culture period, the support matrices were harvested for biochemical and histological analysis. Sulfated glycosaminoglycan production was measured using a modified dimethylmethylene blue microassay. Histological analysis utilized Safranin-O staining. More detailed conditions are to be found in Examples.

The first study was directed to determination of effect of constant (atmospheric), cyclic or constant hydrostatic pressure on production of S-GAG.

At the end of the culture period, both control and test matrices were harvested for biochemical and histological analysis. For biochemical analysis, production of sulfated glycosaminoglycan (S-GAG µg/cell construct) was measured using a modified dimethylmethylene blue (DMB) and DNA microassays described in Example 7. Results are seen in Tables 1 and 2 and FIGS. 3-6.

Results of some studies are seen in Tables 1 and 2 showing a numerical representation of observed increase in S-GAG production in matrices treated with the algorithm of the invention.

TABLE 1

| Group (n = 6) | Pressure Conditions | | Total days in Culture | S-GAG Production (μg/cell construct) (Mean ± SD) |
|---|---|---|---|---|
| | In TESS (3 MPa Cyclic Pressure, @0.5 Hz) | In Incubator (Atmospheric Pressure) | | |
| Initial | — | 0 day | 0 | 12.56 ± 0.99 |
| Control | — | 18 days | 18 | 57.73 ± 6.43 |
| Test | 6 days | 12 days | 18 | *76.32 ± 4.12 |

(*p < 0.05, compared to Control)

Table 1 summarizes results obtained from seeded matrices (n=6) subjected either to atmospheric pressure in an incubator for 18 days (control) or to processing in TESS processor under 3 MPa cyclic hydrostatic pressure at 0.5 Hz for 6 days, followed by 12 days in incubator at atmospheric pressure (test).

Figure 3A:
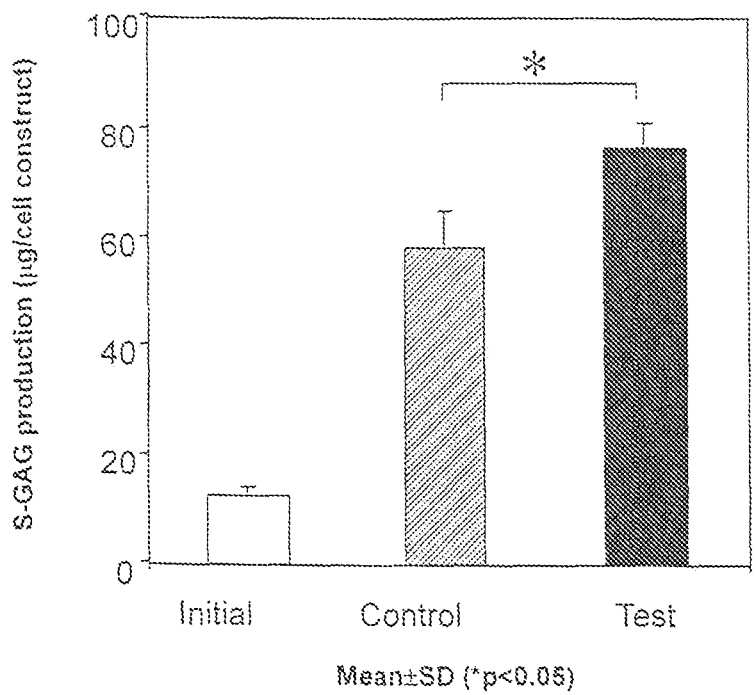
FIG. 3A is a graph representing S-GAG accumulation in cell constructs subjected to static atmospheric (control) or cyclic hydrostatic pressure (test).
Figure 3B:
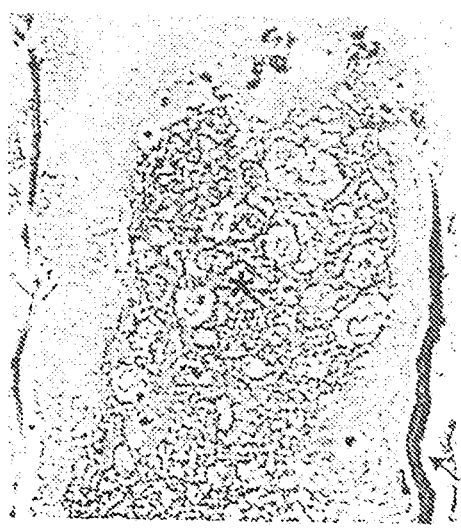
FIG. 3B is a photomicrograph of Safranin-O staining for S-GAG on paraffin sections in 18 days subjected to static pressure.
Figure 3C:
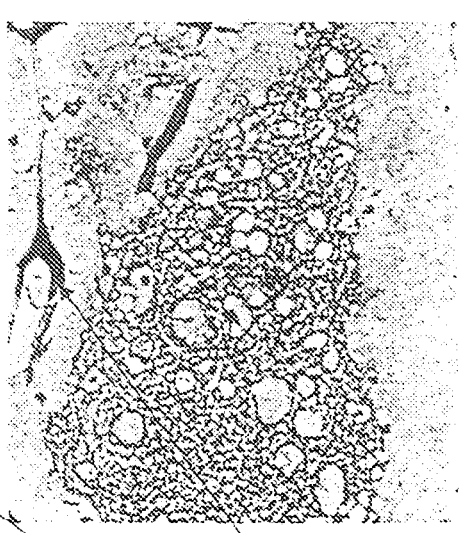
FIG. 3C is a photomicrograph of Safranin-O staining for S-GAG on paraffin sections in cell constructs subjected to cyclic hydrostatic pressure for 6 days followed by 12 days of static pressure.

As seen in Table 1, S-GAG production (μg/cell construct) per seeded matrix was significantly increased to 132% for test compared to 100% control (FIG. 3A). Histological results seen in FIGS. 3B and 3C (Safranin-O staining for S-GAG) were consistent with the results seen in Table 1 obtained biochemically. FIG. 3B is a photomicrograph of Safranin-O staining for S-GAG on paraffin sections in 18 days subjected to static pressure. FIG. 3C is a photomicrograph of Safranin-O staining for S-GAG on paraffin sections in cell constructs subjected to cyclic hydrostatic pressure for 6 days followed by 12 days of static culture.

As seen in FIG. 3B, when the cell constructs are subjected to static atmospheric pressure (FIG. 3B), there is much lower S-GAG accumulation in the constructs than when it is subjected to a cyclic hydrostatic pressure for 6 days, followed by 12 days of static atmospheric pressure (FIG. 3C).

To determine the effect of the hydrostatic pressure on chondrocyte proliferation stimulation and matrix accumulation, cartilage was harvested under sterile conditions as described above. Chondrocytes were expanded for 5 days at 37° C. and suspended in VITROGEN® (300,000/30 μl). The suspension was absorbed into a honeycomb support matrix or collagen sponge as seen in FIG. 1. The cell constructs were incubated in culture medium at 37° C., 5% $CO_2$ and 20% $O_2$, at 0.5 MPa cyclic hydrostatic pressure or 0.5 MPa constant hydrostatic pressure for 6 days followed by incubation for 12 days at atmospheric pressure in the Tissue Engineering Support System (TESS™) processor seen in FIG. 2. The remaining cell matrices comprising the control group were incubated at atmospheric pressure for 18 days at 37° C., 5% $CO_2$ and 20% $O_2$.

At the end of the culture period, the matrices were harvested for biochemical analysis. Results are seen in Table 2. Glycosaminoglycan production was measures using a modified dimethylmethylene blue (DMB) microassay. Cell proliferation was measured using a modified Hoechst Dye DNA assay. Formation of neo-tissue was evaluated by Safranin-O staining. Results are seen in FIGS. 4A, 4B, 5A and 5B and in Table 2.

TABLE 2

| Group (n = 7) | Pressure Conditions | | | | S-GAG GAG Production (μg/cell construct) (Mean ± SD) | DNA |
|---|---|---|---|---|---|---|
| | In TESS | | Days in Incubator (Atmospheric Pressure) | Total days In culture | | DNA Index (Control = 1) |
| | Type of Pressure | Time/ Days | | | | |
| Control | — | — | 18 | 18 | 59.85 ± 7.69 | 1 |
| Cy-HP Cyclic | 0.5 MPa | 6 | 12 | 18 | *91.05 ± 10.68 | 1.49 |
| Const-HP Constant | 0.5 MPa | 6 | 12 | 18 | *97.85 ± 5.53 | 1.74 |

(*p < 0.05, compared to Control)

All cultures were incubated at 37° C., 5% $CO_2$ and 20% $O_2$. In TESS culture, the medium flow rate was 50 μl/min. Two cell matrices from each group were harvested for histological analysis.

As seen in Table 2, the matrices subjected to conditions listed in the control group, cyclic hydrostatic pressure (Cy-HP) and constant hydrostatic pressure (const-HP) groups resulted in production of 59.85, 91.05 and 97.85 μg/cell construct of S-GAG and 1, 1.49 and 1.74 (control=1) of DNA content Index, respectively. These results clearly show that neo-cartilage cultured under hydrostatic pressure, whether cyclic or constant, followed by static culture is more genetically and metabolically active than the neo-cartilage treated under static atmospheric conditions (controls). These results are graphically illustrated in FIG. 4 which shows effect of hydrostatic pressure on production of sulfated glycosaminoglycan (FIG. 4A) and DNA content index (FIG. 4B).

Figure 4A:
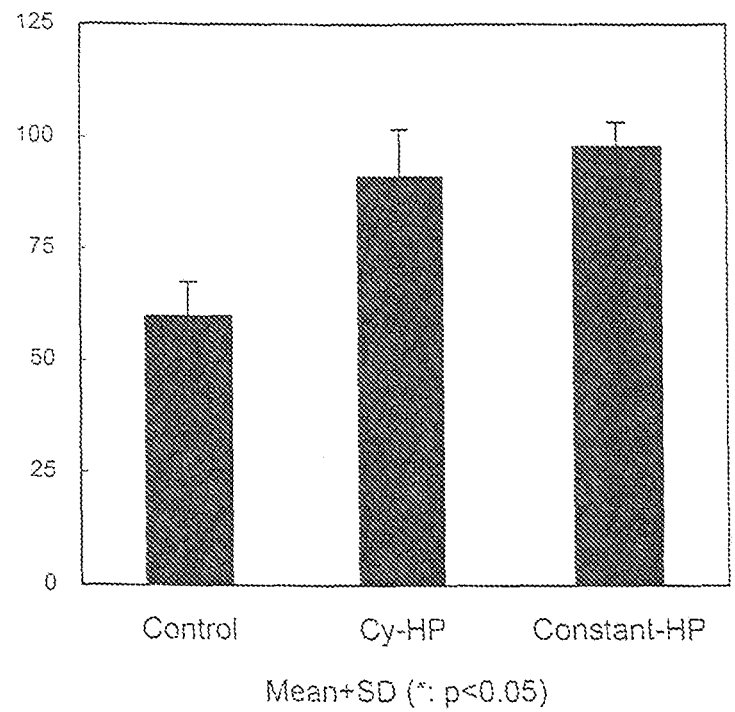
FIG. 4 illustrates effect of cyclic and constant hydrostatic pressure on production of S-GAG (FIG. 4A) and DNA (FIG. 4B).
Figure 4B:
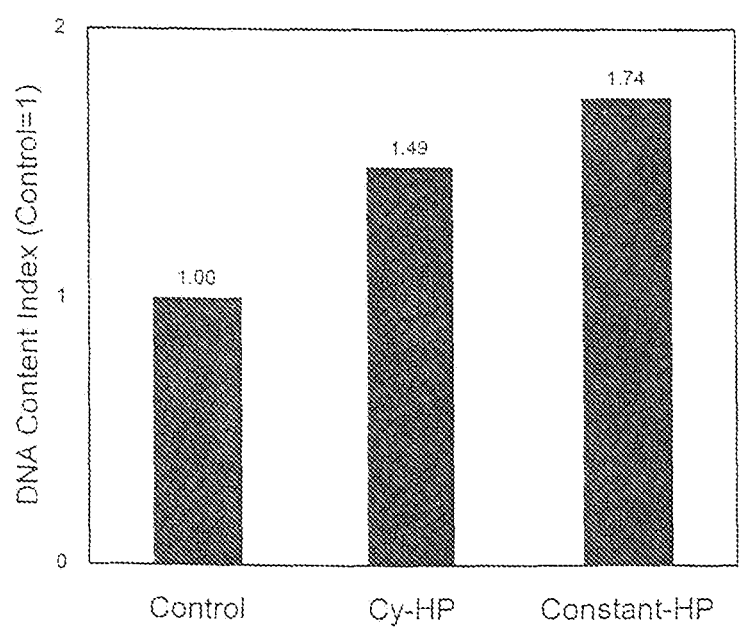

FIG. 4A is a graphical representation of results enumerated in Table 2 and shows the sulfated glycosaminoglycan production in μg/cell construct wherein control represents seeded matrices subjected to atmospheric pressure, Cy-HP represents seeded matrices subjected to cyclic hydrostatic pressure (0.5 MPa) and constant-HP represent matrices subjected to constant hydrostatic pressure (0.5 MPa).

Results seen in Table 2 are illustrated graphically in FIG. 4A, under the conditions described above. There was significant increase in S-GAG production for both the cyclic (Cy-HP) and constant hydrostatic pressure (constant-HP) groups compared to atmospheric pressure (control) group. Specifically, the production of S-GAG in the control group was 59.85

μg/cell construct. In the group Cy-HP the production was 91.05 μg/cell construct. In the group constant-HP cell construct production was 97.85 μg/cell construct resulting in increase of S-GAG production to 152% for group Cy-HP and to 162% for the group constant-HP compared to the control group.

FIG. 4B shows DNA production with corresponding results presented in Table 2 for DNA, likewise showing increased production of DNA in constructs processed under cyclic or constant hydrostatic pressure.

FIG. 5A is a graph comparing effect of constant atmospheric pressure (Control) and zero MPa hydrostatic pressure (0 MPa) serving as pressure controls, 0.5 MPa cyclic hydrostatic pressure (Cy-HP) and 0.5 MPa constant hydrostatic pressure (constant-HP) at day 6 and 18 on support matrices subjected to processing in the TESS processor. All matrices were incubated at 37° C. for 18 days. The Cy-HP and constant-HP were applied for the first 6 days followed by 12 days of incubation at atmospheric pressure.

Results seen in FIG. 5A show that combination of Cy-HP or constant-HP with resting period of atmospheric pressure incubation resulted in significant (p<0.05) increase of S-GAG production in the processed matrices compared to S-GAG production observed in matrices processed at atmospheric pressure with perfusion only.

FIG. 5B shows the index of DNA content (Initial=1) in matrices subjected to static (Control), zero hydrostatic (0 MPa), cyclic (Cy-HP) or constant (Constant-HP) hydrostatic pressure for 6 day and 12 days of atmospheric pressure culture. Increase in DNA content in matrices subjected to the algorithm conditions is clearly shown in both cyclic and constant hydrostatic pressure groups. Comparison of the initial and control DNA level to DNA levels in all three groups subjected to hydrostatic pressure reveals that the DNA level in constructs subjected to the cyclic hydrostatic pressure is higher at day 6 than at day 18 and the DNA level in constructs subjected to constant hydrostatic pressure is lower at day 6 than at day 18. Highest levels of DNA is observed in matrices submitted to constant hydrostatic pressure at day 18.

FIGS. 6A and 6B show histological evaluation of matrices by Safranin-O. FIG. 6A shows accumulation of S-GAG on day 18 in matrices subjected to atmospheric pressure. FIG. 6B shows accumulation of S-GAG in matrices subjected to 6 days of cyclic hydrostatic pressure (Cy-HP), followed by 12 days of atmospheric pressure. The greater S-GAG accumulation in Cy-HP culture matrices is evident from the increased density of the photomicrograph clearly visible in the construct. FIG. 3C shows accumulation of Type II collagen in matrices subjected to the atmospheric pressure or to the cyclic hydrostatic pressure (FIG. 6D). Larger accumulation of Type II collagen in FIG. D is clearly seen.

These results demonstrate that chondrocytes may be placed in culture to coalesce into a neo-cartilage construct with accumulated extracellular matrix macro molecules, such as sulfated glycosaminoglycan (S-GAG).

b) Evaluation of Effect of Perfusion Flow

The second type of study was performed in order to determine the effect of perfusion flow rate on chondrocyte proliferation (DNA content) and production of extracellular matrix (S-GAG accumulation). Results are seen in Table 3 and FIGS. 7A and 7B.

Figure 7A:
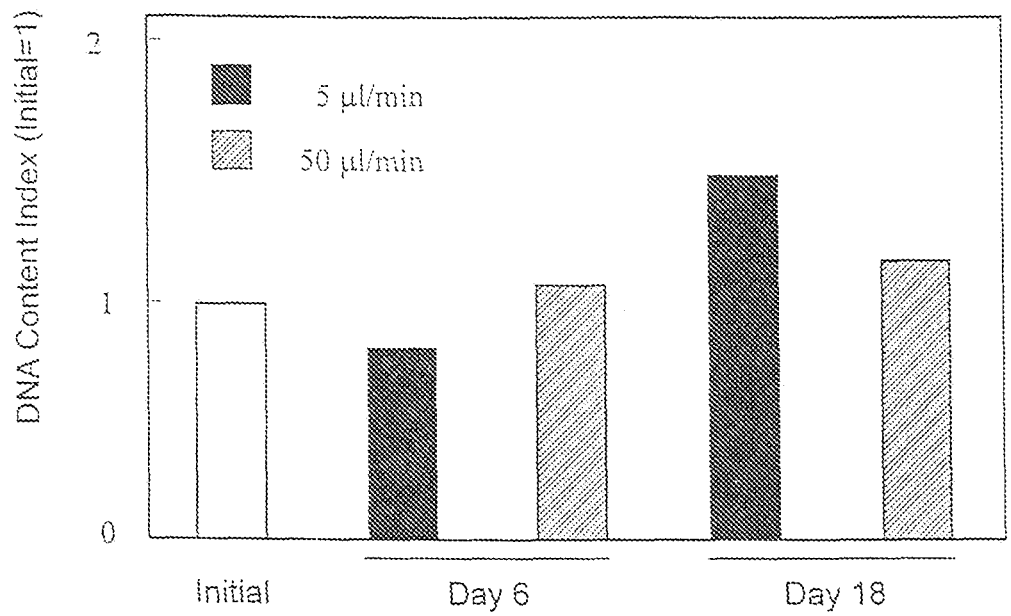
FIG. 7A is a graph illustrating effect of the medium perfusion flow rate on cell proliferation (DNA content) by cell constructs subjected to a medium flow rate of either 0.005 or 0.05 ml/min.
Figure 7B:
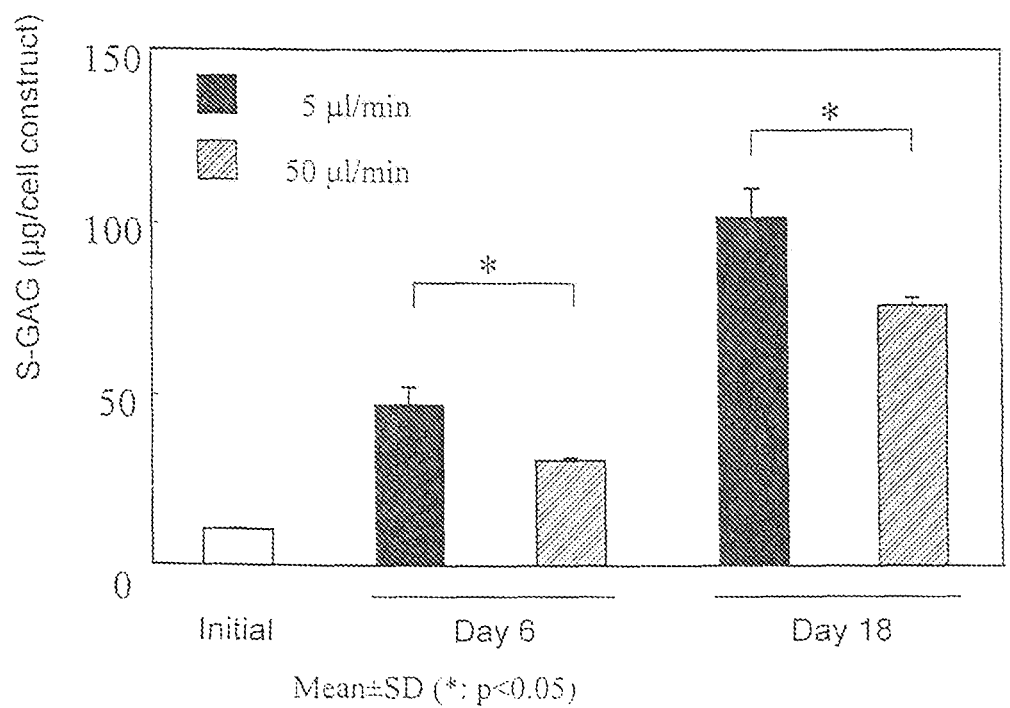
FIG. 7B illustrates effect of flow rate on production of S-GAG.

FIG. 7 describes results of studies of the effect of the perfusion flow rate on cell proliferation measured by levels of DNA content index (FIG. 7A) and, S-GAG accumulation (FIG. 7B) at day 0, 6 and 18.

FIG. 7A shows that the lower perfusion rate (5 μl/min) results in higher DNA content index used as a measure for determination of cell proliferation. Specifically, the DNA content index compared to the initial DNA content index equal to 1 increased by about 50% to about 1.5 when the culture perfusion rate was 5 μl/min. The higher perfusion rate (50 μl/min) resulted in much smaller increase in DNA content index to about 1.2.

Table 3 shows the effect of perfusion flow rate on the S-GAG production in matrices treated as outlined above where the flow rate was either 0.05 mL/min (50 μl/min) or 0.005 mL/min (5 μl/min).

TABLE 3

| Group (n = 7) | Medium Perfusion Flow Rate (mL/min) | Culture duration | | Total days in culture | GAG Production (μg/cell construct) (Mean ± SD) |
| | | In TESS (0.5 MPa Cyclic Pressure) | In Incubator (Atmospheric Pressure) | | |
|---|---|---|---|---|---|
| A | 0.05 mL/min | 6 days | 12 days | 18 days | 78.75 ± 6.84 |
| B | 0.005 mL/min | 6 days | 12 days | 18 days | 107.33 ± 8.53 |

All cultures were incubated at 37° C., 5% $CO_2$ and 20% $O_2$. In the culture, 0.5 MPa cyclic pressure at 0.5 Hz was applied to the cell matrices. Two matrices from each group were harvested for histological analysis.

As seen in Table 3, the lower perfusion rate (5 μl/min) resulted in approximately 1.5 higher production of S-GAG than the higher perfusion rate (50 μl/min).

These results are seen in graphical form in FIG. 7B. FIG. 7B is graph showing differences between S-GAG production by seeded support matrices subjected to a medium perfusion flow rate of 5 μl/min compared to matrices subjected to a medium perfusion flow rate of 50 μl/min at days 6 and 18. As seen in FIG. 7B, increase in S-GAG production up to 136% (p<0.05) in matrices subjected to a slower rate of 5 μl/min.

The results summarized in FIGS. 7A and 7B clearly show a significant increase in both the DNA content index and S-GAG production in the cell construct at a flow rate of 5 μl/min compared to the flow rate 50 μl/mL. There is no significant difference in the amount of S-GAG released into the medium between the two flow rates. It is therefore possible to use lower flow rate and avoid shear.

Determination whether the combination of the perfusion flow rate with cyclic or constant hydrostatic pressure leads to increased formation of extracellular matter was also studied. Results are seen in FIG. 8.

Figure 8C:
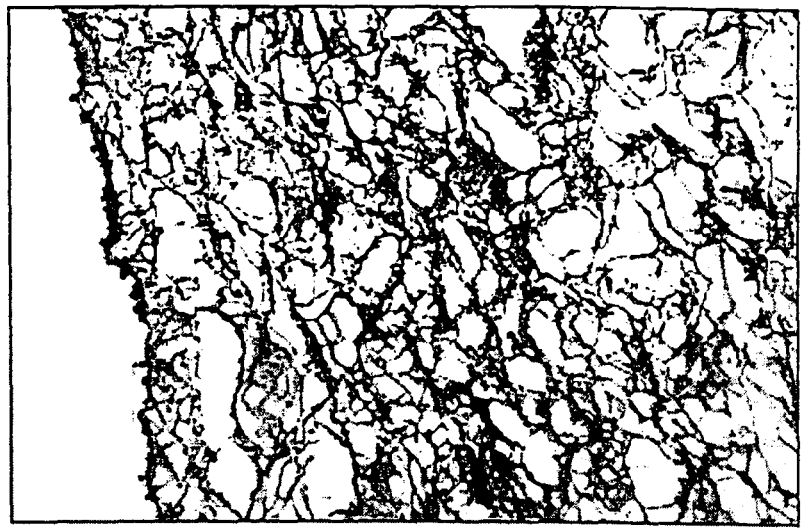
FIG. 8 shows accumulation detected histologically by toluidine S-GAG blue staining after 15 days culture submitted to perfusion (FIG. 8A), cyclic hydrostatic pressure (FIG. 8B) and constant hydrostatic pressure (FIG. 8C).
Figure 8B:
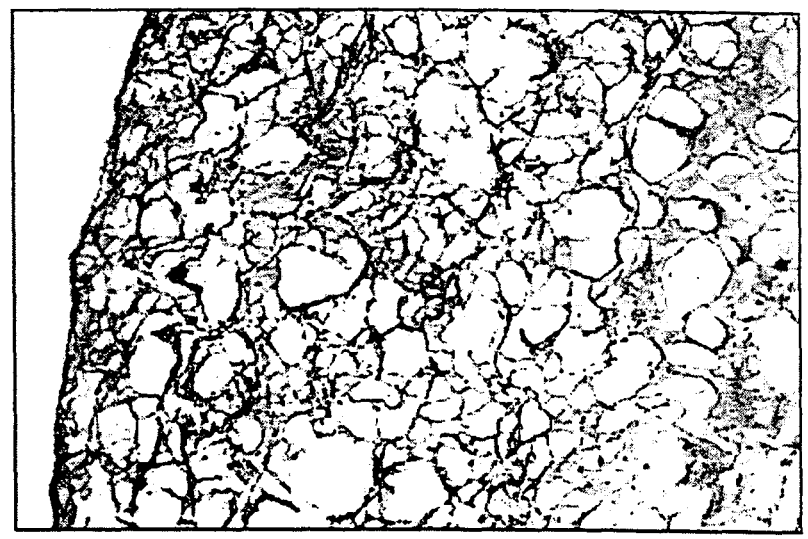
Figure 8A:
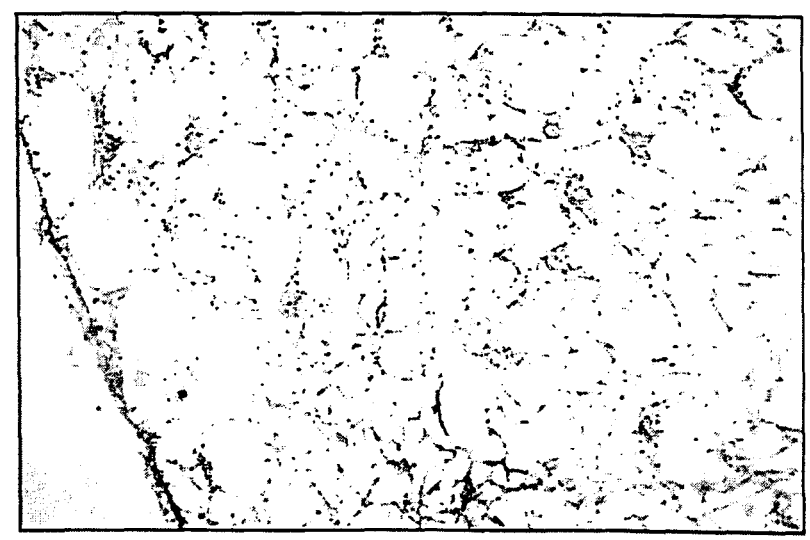

FIG. 8 illustrates a formation of extracellular matrix after 15 days culture determined in matrices treated with perfusion (5 μl/min) only (FIG. 8A), cyclic hydrostatic pressure 2.8 MPa at 0.015 Hz (FIG. 8B) and constant hydrostatic pressure 2.8 MPa at 0.015 Hz (FIG. 8C) as determined by toluidine blue staining. This figure clearly shows that hydrostatic pressure and medium perfusion enhances production of extracellular matrix.

C. Evaluation of Effect of Low Oxygen Tension

The third type of study was performed in order to determine the effect of low oxygen tension on chondrocyte proliferation (DNA content) and production of extracellular matrix (S-GAG accumulation). Results are seen in Table 4 and FIGS. 9A and 9B.

TABLE 4

|  |  | Culture duration | | | |
| --- | --- | --- | --- | --- | --- |
| Group (n = 8) | Oxygen concentration (%) | In TESS (0.5 MPa Cyclic Pressure) | In Incubator (Atmospheric Pressure) | Total days in culture | GAG Production (µg/cell construct) (Mean ± SD) |
| A | 20% | 7 days | 14 days | 21 days | 60.89 ± 6.02 |
| B | 2% | 7 days | 14 days | 21 days | *105.59 ± 10.95 |

(*p < 0.05, compared to group A)

All cultures were incubated at 37° C., at 5% $CO_2$. In TESS culture, the medium flow rate was 5 µl/min. Two cell matrices from each group were harvested for histological analysis.

As seen in Table 4, the lower oxygen tension (2% $O_2$ concentration) resulted in approximately 1.7 higher production of S-GAG than higher oxygen concentration (20%) corresponding to atmospheric $O_2$ concentration. These results are seen in graphical form in FIG. 9A.

Figure 9A:
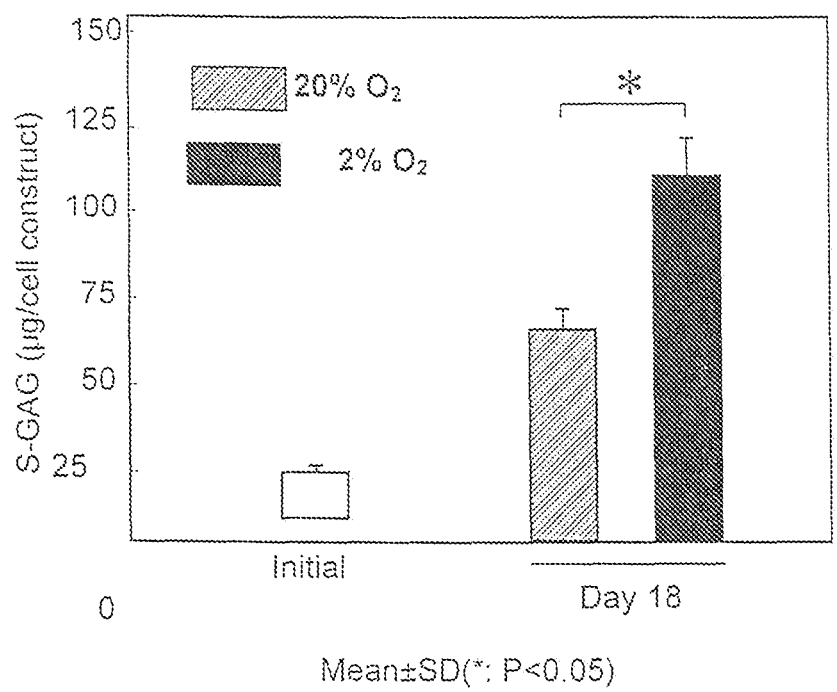
FIG. 9 illustrates effect of low oxygen tension on S-GAG production (FIG. 9A) and cell proliferation (FIG. 9B).

FIG. 9A is a graph showing differences between S-GAG production by cell constructs subjected to 2% oxygen concentration (Cy-HP) and to cyclic hydrostatic pressure followed by static pressure compared to cell constructs subjected to 20% oxygen concentration and Cy-HP followed by static pressure. As already seen in Table 4, at 2% oxygen concentration compared to 20% concentration, the production of S-GAG rose by approximately 70%.

Figure 9B:
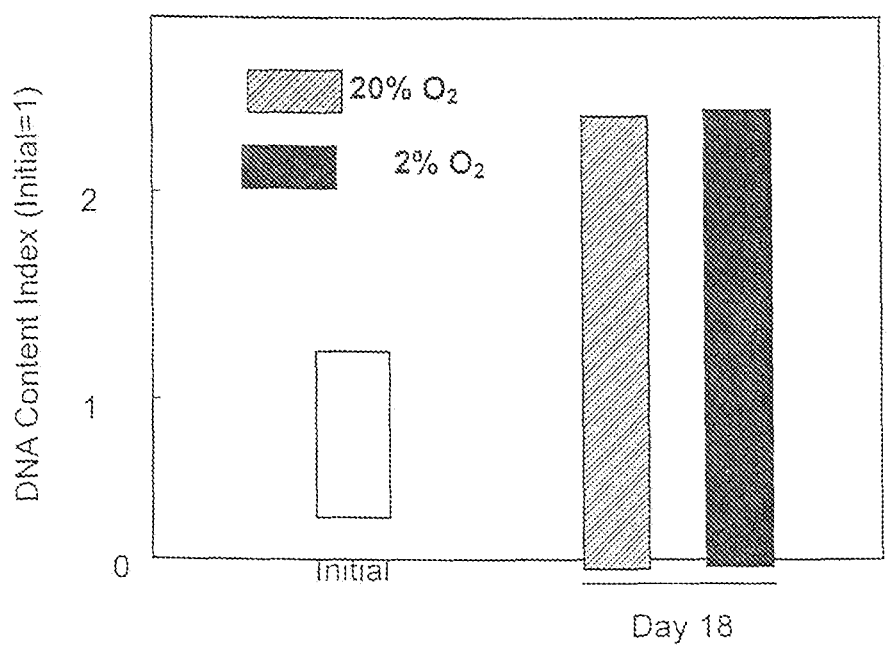

FIG. 9B shows the DNA content index (initial=1) in cell constructs subjected to 2% or 20% oxygen concentration and Cy-HP pressure followed by static pressure. There are no significant differences in the DNA content index between 2% oxygen concentration and 20% oxygen concentration. These results indicate that the lower oxygen tension stimulates S-GAG production in cell constructs when combined with the cyclic hydrostatic culture followed by static culture. However, the cell proliferation, expressed as DNA content index, is not affected by changes in oxygen tension.

The algorithm of the invention thus comprises at least a combination of the low perfusion flow rate from about 1 to 500 µL/minute, preferably about 5 to 50 µL/minute, most preferably about 5 µL/minute, low oxygen concentration from about 1% to about 20%, preferably about 2% to about 5%, with a certain predetermined period of cyclic or constant hydrostatic pressure from zero to about 10 MPa at about 0.01 to about 1 Hz, preferably about 0.1 to about 0.5 Hz, from about zero to about 10 MPa of cyclic or constant hydrostatic pressure, preferably about 0.05 MPa to about 3 MPa at about 0.1 to about 0.5 Hz, followed by the period of a static atmospheric pressure. The algorithm conditions are applied from about 1 hour to about 90 days wherein the time for applying the hydrostatic pressure is from zero to about 24 hours per day for from about one day to about ninety days, wherein said hydrostatic pressure is preceded or followed by a period of zero to about 24 hours of a static atmospheric pressure for from about one day to about ninety days with preferred time for applying the hydrostatic cyclic or constant pressure of about 7 to 28 days followed or preceded by a period of zero to about 28 days of the atmospheric pressure.

d) General Applicability of the Algorithm of the Invention to Various Cell Types The algorithm described above for chondrocytes is similarly applicable to other types of cell and tissue, such as fibroblasts, fibrochondrocytes, tenocytes, osteoblasts and stem cells capable of differentiation, or tissues such as cartilage connective tissue, fibrocartilage, tendon and bone. The algorithm conditions may be the same or different but would be generally within the above described ranges.

II. Neo-Cartilage Composition Construct

The neo-cartilage composition construct is a multilayered three-dimensional structure comprised at least of living chondrocytes incorporated into a cellular support matrix. The support matrix is embedded with living chondrocytes.

The construct is fabricated in vitro and ex vivo prior to implanting into the cartilage lesion. The construct is fabricated using the method and conditions, cumulatively called the algorithm, described above, with all conditions being variable within the given ranges and depending on the intended use or on the method of delivery.

In one embodiment, the autologous or heterologous chondrocytes are cultured as described, embedded into the support matrix and processed into the neo-cartilage construct using predetermined medium perfusion flow rate, cyclic or constant hydrostatic pressure and reduced or increased concentration of oxygen and/or carbon dioxide. The neo-cartilage construct is delivered into the cartilage lesion cavity and deposited between two layers of sealant and left in situ to be integrated into the native cartilage.

III. Method for Formation of Superficial Cartilage Layer

The primary aspect of this invention is a finding that when the neo-cartilage, neo-cartilage construct or seeded support matrix produced according to procedures and conditions described above is implanted into a cartilage lesion cavity and covered with a biocompatible adhesive sealant, the resulting combination leads to a formation of a superficial cartilage layer completely overgrowing said lesion.

The method is based on producing a neo-cartilage and neo-cartilage construct comprising support matrix seeded with expanded chondrocytes processed according to the algorithm of the invention. Chondrocytes are typically suspended in a collagen sol which is thermo-reversible and easily changes from sol to gel at the body temperature thereby permitting external preparation of and delivery of the neo-cartilage construct into the lesion in form of the sol which changes its state into gel upon delivery to the lesion and warming to the body temperature.

The neo-cartilage construct is implanted into the lesion and covered by a layer of a biologically acceptable adhesive sealant. Optionally, the first layer of the sealant is introduced into the lesion and deposited at the bottom of the lesion. This first sealant's function is to prevent entry and to block the migration of subchondral and synovial cells of the extraneous components, such as blood-borne agents, cell and cell debris, etc., into the cavity and their interference with the integration of the neo-cartilage therein. The second sealant layer is placed over the surface of the construct. The presence of both these sealants in combination with the neo-cartilage construct results in successful integration of the neo-cartilage into the joint cartilage.

The method may be practiced in several modes and each mode involves generic steps outlined below in variable combinations.

General way to practice the method for repair and restoration of damaged, injured, diseased or aged cartilage to a functional cartilage is to follow steps:

a) Preparing Neo-Cartilage, Neo-Cartilage Construct or Chondrocyte Support Matrix This step involves preparation of neo-cartilage, neo-cartilage comprising constructs and support matrix comprising autologous or heterologous chondrocytes incorporated therein. Preparation of any of the three entities named above is described in greater detail above in sections I.B-D.

b) Depositing the First and Second Sealant into the Lesion

This step involves introducing a first and a second layer of a first and a second biologically acceptable sealant into a cartilage lesion. The first and second sealants may be the same or different. It is to be understood that the utilization of the first bottom layer is optional and that the method for a formation of the superficial cartilage layer is enabled without the first layer.

Specifically, this step involves deposition of the first sealant at the bottom of the lesion and of the second sealant over the lesion. The first and the second sealants can be the same or different, however, both the first and the second sealants must have certain definite properties to fulfill their functions.

The first sealant, deposited into the cavity before the neo-cartilage is deposited, acts as a protector of the lesion cavity integrity, that is, it protects the lesion cavity not only from extraneous substances but it also protect this cavity from formation of the fibrocartilage in the interim when the cavity is filled with a space-holding gel in expectation of implantation of the neo-cartilage after processing. The second sealant acts as a protector of the lesion cavity on the outside as well as a protector of the neo-cartilage construct deposited within a cavity formed between the two sealants and as well as an initiator of the formation of the superficial cartilage layer.

1. First Sealant

The optionally deposited first sealant forms an interface between the introduced neo-cartilage construct and the native cartilage. The first sealant, deposited at the bottom of the lesion, must be able to protect the construct from and prevent chondrocyte migration into the sub-chondral space. Additionally, the first sealant prevents the infiltration of blood vessels and undesirable cells and cell debris into the neo-cartilage construct and it also prevents formation of the fibrocartilage.

2. Second Sealant

The second sealant acts as a protector of the neo-cartilage construct or the lesion cavity on the outside and is typically deposited over the lesion either before or after the neo-cartilage is deposited therein and in this way protects the integrity of the lesion cavity from any undesirable effects of the outside environment, such as invading cells or degradative agents and seals the space holding gel in place before the neo-cartilage is deposited therein. The second sealant also acts as a protector of the neo-cartilage construct implanted within a cavity formed between the two sealants. In this way, the second sealant may be deposited after the neo-cartilage is implanted over the first sealant and seal the neo-cartilage within the cavity or it may be deposited over the space holding gel. The third function of the second sealant is as an initiator or substrate for the formation of a superficial cartilage layer. Studies performed during the development of this invention discovered that when the second sealant was deposited over the cartilage lesion, a growth of the superficial cartilage layer occurred as an extension of the native superficial cartilage layer. This superficial cartilage layer is particularly well-developed when the lesion cavity is filled with the space-holding or thermo-reversible gel thereby leading to the conclusion that such a gel might provide a substrate for the formation of such superficial cartilage layer.

3. First and Second Sealant Properties

The first or second sealant of the invention must possess the following characteristics:

Sealant must be biologically acceptable, easy to use and possess required adhesive and cohesive properties.

The sealant is biologically compatible with tissue, be non-toxic, not swell excessively, not be extremely rigid or hard, as this could cause abrasion of or extrusion of the sealant from the tissue site, must not interfere with the formation of new cartilage, or promote the formation of other interfering or undesired tissue, such as bone or blood vessels and must resorb and degrade by an acceptable pathway or be incorporated into the tissue.

The sealant must rapidly gel from a flowable liquid or paste to a load-bearing gel within 3 to 15 minutes, preferably within 3-5 min. Longer gelation times are not compatible with surgical time constraints. Additionally, the overall mode of use should be relatively simple because complex procedures will not be accepted by surgeons.

Adhesive bonding is required to attach the sealant formulation to tissue and to seal and support such tissue. Minimal possessing peel strengths of the sealant should be at least 3N/m and preferably 10 to 30 N/m. Additionally, the sealant must itself be sufficiently strong so that it does not break or tear internally, i.e., it must possess sufficient cohesive strength, measured as tensile strength in the range of 0.2 MPa, but preferably 0.8 to 1.0 MPa. Alternatively, a lap shear measurement may be given to define the bond strength of the formulation should have values of at least 0.5 $N/cm^2$ and preferably 1 to 6 $N/cm^2$.

Sealants possessing the required characteristics are typically polymeric. In the un-cured, or liquid state, such sealant materials consist of freely flowable polymer chains which are not cross-linked together, but are neat liquids or are dissolved in physiologically compatible aqueous buffers. The polymeric chains also possess side chains or available groups which can, upon the appropriate triggering step, react with each other to couple, or cross-link the polymer chains together. If the polymer chains are branched, i.e., comprising three or more arms on at least one partner, the coupling reaction leads to the formation of a network which is infinite in molecular weight, i.e., a gel.

The formed gel has cohesive strength dependent on the number of inter-chain linkages, the length (molecular weight) of the chains between links, the degree of inclusion of solvent in the gel, the presence of reinforcing agents, and other factors. Typically, networks in which the molecular weight of chain segments between junction points (cross-link bonds) is 100-500 Daltons are tough, strong, and do not swell appreciably. Networks in which the chain segments are 500-2500 Daltons swell dramatically in aqueous solvents and become mechanically weak. In some cases the latter gels can be strengthened by specific reinforcer molecules; for example, the methylated collagen reinforces the gels formed from 4-armed PEGs of 10,000 Daltons (2500 Daltons per chain segment).

The gel's adhesive strength permits bonding to adjacent biological tissue by one or more mechanisms, including electrostatic, hydrophobic, or covalent bonding. Adhesion can also occur through mechanical inter-lock, in which the uncured liquid flows into tissue irregularities and fissures, then, upon solidification, the gel is mechanically attached to the tissue surface.

At the time of use, some type of triggering action is required. For example, it can be the mixing of two reactive partners, it can be the addition of a reagent to raise the pH, or it can be the application of heat or light energy.

Once the sealant is in place, it must be non-toxic to adjacent tissue, and it must be incorporated into the tissue and retained permanently, or removed, usually by hydrolytic or enzymatic degradation. Degradation can occur internally in the polymer chains, or by degradation of chain linkages, followed by diffusion and removal of polymer fragments dissolved in physiological fluids.

Another characteristic of the sealant is the degree of swelling it undergoes in the tissue environment. Excessive swelling is undesirable, both because it creates pressure and stress locally, and because a swollen sealant gel loses tensile strength, due to the plasticizing effect of the imbibed solvent (in this case, the solvent is physiological fluid). Gel swelling is modulated by the hydrophobicity of the polymer chains. In some cases it may be desirable to derivatize the base polymer of the sealant so that it is less hydrophilic. For example, one function of methylated collagen containing sealant is presumably to control swelling of the gel. In another example, the sealant made from penta-erythritol tetra-thiol and polyethylene glycol diacrylate can be modified to include polypropylene glycol diacrylate, which is less hydrophilic than polyethylene glycol. In a third example, sealants containing gelatin and starch can also be methylated both on the gelatin and on the starch, again to decrease hydrophilicity.

4. Suitable and Non-Suitable Sealants

Sealants suitable for purposes of this invention include the sealants prepared from gelatin and di-aldehyde starch triggered by mixing aqueous solutions of gelatin and dialdehyde starch which spontaneously react and gel. The gel bonds to tissue through a reaction of aldehyde groups on starch molecules and amino groups on proteins of tissue, with an adhesive bond strength to up to 100 N/m and an elastic modulus of 8×106 Pa, which is a characteristic of a relatively tough, strong material. After swelling in physiological fluids this cohesive strength declines. The gelled sealant is degraded by enzymes that cleave the peptide bonds of gelatin and the glycosidic bonds of starch.

Another acceptable sealant is made from a copolymer of polyethylene glycol and poly-lactide or -glycolide, further containing acrylate side chains and gelled by light, in the presence of some activating molecules. The linkage is formed by free-radical chemistry. The gel bonds to tissue by mechanical interlock, having flowed into tissue surface irregularities prior to curing. The sealant degrades from the tissue by hydrolytic cleavage of the linkage between polyethylene glycol chains, which then dissolve in physiological fluids and are excreted.

The acceptable sealant made from periodate-oxidized gelatin remains liquid at acid pH, because free aldehyde and amino groups on the gelatin cannot react. To trigger gelation, the oxidized gelatin is mixed with a buffer that raises the pH, and the solution gels. Bonding to tissue is through aldehyde groups on the gelatin reacting with amino groups on tissue. After gelation, the sealant can be degraded enzymatically, due to cleavage of peptide bonds in gelatin.

Still another sealant made from a 4-armed pentaerythritol thiol and a polyethylene glycol diacrylate is formed when these two neat liquids (not dissolved in aqueous buffers) are mixed. The rate of gelation is controlled by the amount of a catalyst, which can be a quaternary amino compound, such as tri-ethanolamine. A covalent linkage is formed between the thiol and acrylate, to form a thio-ether bond. The final gel is firm and swells very little. The tensile strength of this gel is high, about 2 MPa, which is comparable to that of cyanoacrylate acceptable Superglue. Degradation of such gels in vivo is slow. Therefore, the gel may be encapsulated or incorporated into tissue.

Another example is the composition, preferred for use in this invention, that contains 4-armed tetra-succinimidyl ester or tetra-thiol derivatized PEG, plus methylated collagen. The reactive PEG reagents in powder form are mixed with the viscous, fluid methylated collagen (previously dissolved in water); this viscous solution is then mixed with a high pH buffer to trigger gelation. The tensile strength of this cured gel is about 0.3 MPa. Degradation presumably occurs through hydrolytic cleavage of ester bonds present in the succinimidyl ester PEG, releasing the soluble PEG chains which are excreted.

In general, a sealant useful for the purposes of this application has adhesive, or peel strengths at least 10N/m and preferably 100 N/cm; it needs to have tensile strength in the range of 0.2 MPa to 3 MPa, but preferably 0.8 to 1.0 MPa. In so-called "lap shear" bonding tests, values of 0.5 up to 4-6 N/cm$^2$ are characteristic of strong biological adhesives.

Such properties can be achieved by a variety of materials, both natural and synthetic. Examples include: 1) gelatin and di-aldehyde starch (International Patent Publication Number WO 97/29715; 21 Aug. 1997); 2) 4-armed penta-erythritol tetra-thiol and polyethylene glycol diacrylate (International Patent Application Number WO 00/44808; 3 Aug. 2000; example 14); 3) photo-polymerizable polyethylene glycol-co-poly(a-hydroxy acid)diacrylate macromers (U.S. Pat. No. 5,410,016; Apr. 25, 1995); 4) periodate-oxidized gelatin (U.S. Pat. No. 5,618,551, Apr. 8, 1997); 5) serum albumin and di-functional polyethylene glycol derivatized with maleimidyl, succinimidyl, phthalimidyl and related active groups (International Patent Publication Number WO 96/03159, Feb. 8, 1996) and 6) 4-armed polyethylene glycols derivatized with succinimidyl ester and thiol, plus methylated collagen, referred to as "CT3" (U.S. Pat. No. 6,312,725 B1, Nov. 6, 2001).

Various other sealant formulations are available commercially or are described in the literature. However, the majority of these are not suitable for practicing this invention for a variety of reasons.

For example, fibrin sealant is unsuitable because it interferes with the formation of cartilage.

Cyanoacrylate, or Superglue, is extremely strong but it might exhibit toxic reactions in tissue.

Un-reinforced hydrogels of various types typically exhibit tensile strengths of lower than 0.02 MPa, which is too weak to support the adhesion required for the purpose of this application because such gels will swell too much, tear too easily, and break down too rapidly.

It is worth noting that it is not the presence or absence of particular protein or polymer chains, such as gelatin or polyethylene glycol, which necessarily govern the mechanical strength and degradation pattern of the sealant. The mechanical strength and degradation pattern are controlled by the cross-link density of the final cured gel, by the types of degradable linkages which are present, and by the types of modifications and the presence of reinforcing molecules, which may affect swelling or internal gel bonding.

5. Preferred Sealants

The first or second sealant of the invention must be a biologically acceptable, typically rapidly gelling synthetic compound having adhesive, bonding and/or gluing properties, and is typically a hydrogel, such as derivatized polyethylene glycol (PEG) which is preferably cross-linked with a collagen compound, typically alkylated collagen. Sealant should have a tensile strength of at least 0.3 MPa. Examples of suitable sealants are tetra-hydrosuccinimidyl or tetra-thiol derivatized PEG, or a combination thereof, commercially available from Cohesion Technologies, Palo Alto, Calif. under the trade name CoSeal™, described in *J. Biomed. Mater. Res (Appl. Biomater.)*, 58:545-555 (2001). Other compounds suitable to be used are the rapid gelling biocompatible polymer compositions described in the U.S. Pat. No. 6,312,725 B1, herein incorporated by reference. Additionally, the sealant may be two or more-part polymers compositions that rapidly form a matrix where at least one of the compounds is polymer, such as, polyamino acid, polysaccharide, polyalkylene oxide or polyethylene glycol and two parts are linked through a covalent bond and cross-linked PEG with methyl collagen, commercially available.

The sealant of the invention typically gels rapidly upon contact with tissue, particularly with tissue containing collagen. The second sealant may or may not be the same as the first sealant. Both the first and the second is preferably a cross-linked polyethylene glycol hydrogel with methyl-collagen, which has adhesive properties.

c) Implanting the Neo-Cartilage Construct

Next step in the method of the invention comprises implanting said neo-cartilage into a lesion cavity formed under the second sealant or between two layers of sealants, said cavity either filled with neo-cartilage construct deposited therein or, optionally, with a space holding thermo-reversible gel (SHTG) deposited into said cavity as a sol at temperatures between about 5 to about 30° C. wherein, within said cavity and at the body temperature, said SHTG converts the sol into gel and in this form the SHTG holds the space for introduction of the neo-cartilage construct and provides protection for the neo-cartilage and wherein its presence further promotes in situ formation of de novo superficial cartilage layer covering the cartilage lesion.

The above step is versatile in that the neo-cartilage may be deposited into said lesion cavity after the first sealant is deposited but before the second sealant is deposited over it or the first and second sealants may be deposited first and the cavity is filled with the space-holding thermo-reversible gel for the interim period when the neo-cartilage is cultured and processed or it may be deposited into the lesion cavity without the first sealant and covered with the second sealant.

The neo-cartilage is either autologous or heterologous and is prepared as described above in sections I.B. a-c.

d) Removing the Space-Holding or Thermo-Reversible Gel from the Lesion Cavity The neo-cartilage is deposited into the cavity either before or after the formation of the superficial cartilage layer. In all cases when the first sealant is used, the first sealant is deposited first. In one embodiment, the neo-cartilage construct containing, typically, the heterologous neo-cartilage might be deposited on the top of the first sealant layer and immediately covered by the second sealant layer. In such an instance, the neo-cartilage is left in the cavity until the superficial cartilage layer is formed and the neo-cartilage is integrated into the surrounding cartilage. Then, depending on the material used for neo-cartilage construct, the sponge gel or thermo-reversible gelling hydrogel are left in the cavity to disintegrate.

In the instance when the two sealants are deposited first, the space within the lesion cavity is optionally filled with a polymer gel, such as the space-holding thermo-reversible gel. Such gel is left in the cavity until the neo-cartilage construct is cultured, processed and ready to be implanted. Since such thermo-reversible gel might or might not be completely or partially degraded during this time, it may be removed from the cavity by cooling the lesion to about 5° C. at which temperature the gel becomes a sol, and by removing said sol from the cavity, for example, by injection. Using the same process, that is by cooling the solid gel of the neo-cartilage, the process may be reversed for introduction of the neo-cartilage construct into said lesion cavity wherein, after the sol is warmed into the body temperature, the sol is converted into a solid gel.

Thus, the primary premise of this process is that the removal and/or introduction of the space holding gel or introduction of neo-cartilage construct proceeds at the cold temperature where the composition is in the sol state and converts into solid gel at warmer temperatures. In this way the gel may be removed from the cavity as the sol after the neo-cartilage integration and formation of superficial cartilage layer.

e) Generation of the Superficial Cartilage Layer

A combination of the neo-cartilage construct comprising the neo-cartilage suspended in the thermo-reversible gel or support matrix embedded with chondrocytes with the adhesive polymeric second sealant leads to overgrowth and complete or almost complete sealing of the lesion cavity.

In alternative, depending on the surface chemistry of the thermo-reversible gel, the superficial layer could grow directly over the neo-cartilage construct if such surface chemistry is propitious to such growth.

Typically, a biologically acceptable second sealant, preferably a cross-linked PEG hydrogel with methyl collagen sealant, is deposited either over the neo-cartilage construct implanted into the lesion cavity or is deposited over the lesion before the neo-cartilage construct is deposited therein. The second sealant acts as an initiator for formation of the superficial cartilage layer which in time completely overgrows the lesion. The superficial cartilage layer in several weeks or months completely covers the lesion and permits integration of the neo-cartilage of the neo-cartilage construct or chondrocytes embedded within the support matrix into the native surrounding cartilage substantially without formation of fibrocartilage.

Formation of the superficial cartilage layer is a very important aspect of the healing of the cartilage and its repair and regeneration.

IV. In vivo Studies in Swine of Weight-Bearing Region of the Knee

The method according to the invention was tested and confirmed in in vivo studies wherein the generation of the superficial cartilage layer has been confirmed in a three month study performed in a swine model in order to evaluate porcine neo-cartilage construct integration into the surrounding cartilage.

The neo-cartilage construct prepared according to the method of the invention was implanted into an artificially generated lesion in a pig's knee. Detailed conditions of the study are described in Example 8. Results of this study are illustrated in FIGS. 10, 11 and 12 depicting histological evaluation using Safranin-O staining method of artificially created cartilage lesions.

Briefly, the study comprised of an open arthrotomy of the right knee joint performed on all animals. A biopsy of the cartilage was obtained. Chondrocytes were isolated from the cartilage biopsy and cultured within a collagen matrix in a Tissue Engineering Support System (TESS™) as described in detail above to produce porcine neo-cartilage construct for subsequent implantation.

Figure 10A:
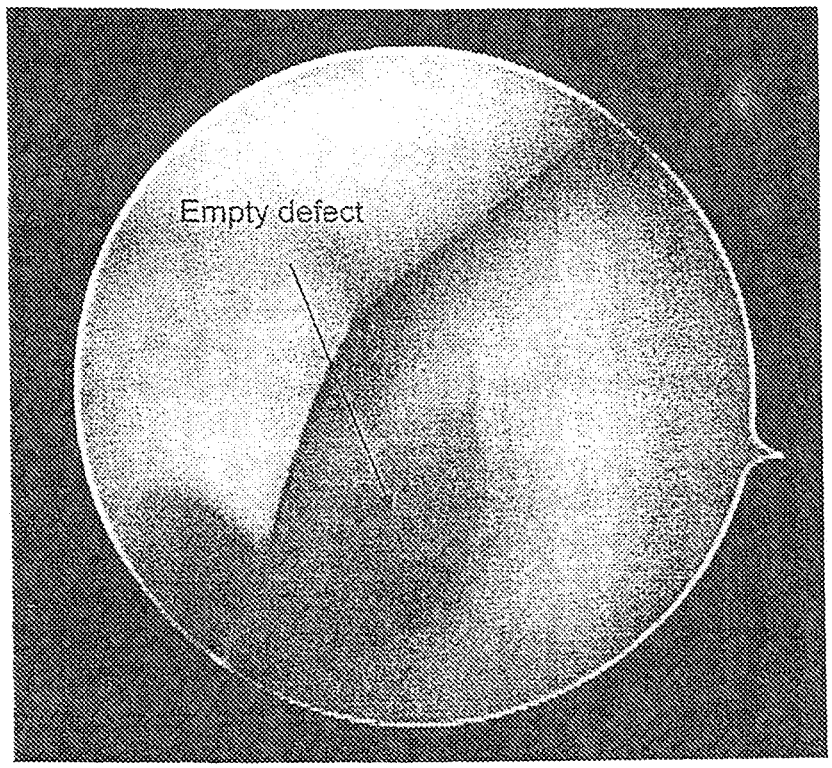
FIG. 10A shows an arthroscopic observation of the control empty defect site 2 weeks after creating empty defect.
Figure 10B:
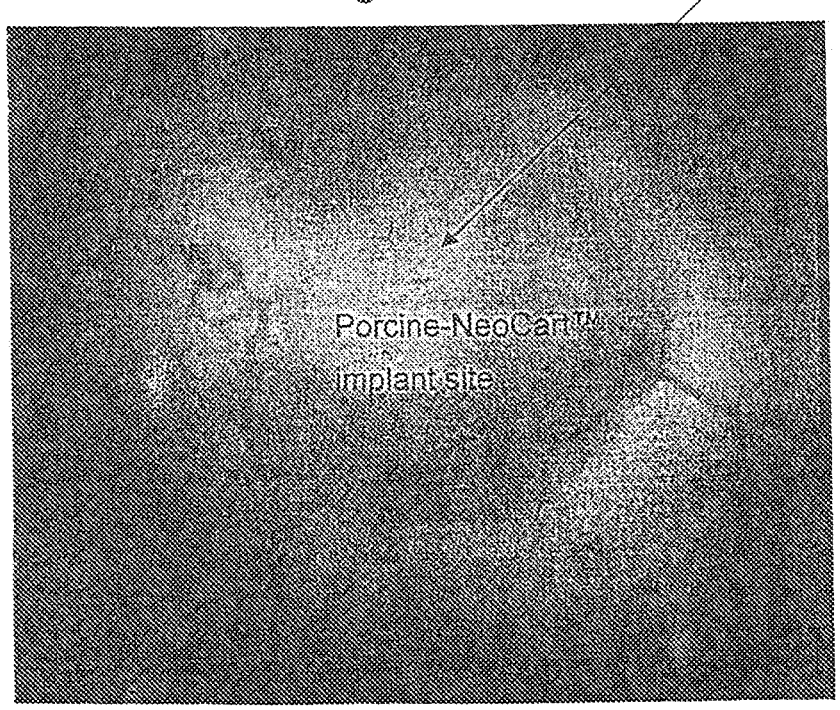
FIG. 10B shows an arthroscopic observation of the porcine neo-cartilage (Porcine-NeoCart™) implant site 2 weeks after the implantation.

A defect was created in the medial femoral condyle of the right knee. This defect, which served as a control, was not implanted with the neo-cartilage construct. The empty defect is seen in FIG. 10A. Following surgery, the joint was immobilized with an external fixation device for a period of about two weeks. Three weeks after the arthrotomy on the right knee was performed, an open arthrotomy was performed on the left knee and the same defects were created in this medial femoral condyle. The porcine neo-cartilage was implanted within defects in this knee which was similarly immobilized. The porcine implant site is seen in FIG. 10B which also show initiation of formation of a superficial cartilage layer two weeks after implantation.

The operated sites were periodically viewed via arthroscopy at monthly intervals. Subsequently, approximately 3 months after porcine neo-cartilage implantation, animals were euthanized and joints harvested and prepared for histological examination. The implanted sites were prepared and examined histologically. Comparison of FIG. 11 (control at four months after arthrotomy) and FIG. 12 shows test knee three month following arthrotomy and neo-cartilage implantation according to the invention. This figure shows that in the control knee there is a visible formation of fibrocartilage. In the test group (FIGS. 12A-12D), the implanted porcine neo-cartilage construct resulted in production of dense regenerating hyaline cartilage and in the same test group, there was clearly visible cell integration (FIGS. 12C and 12D) and formation of the superficial cartilage layer (FIGS. 12A and 12B).

Figure 11A:
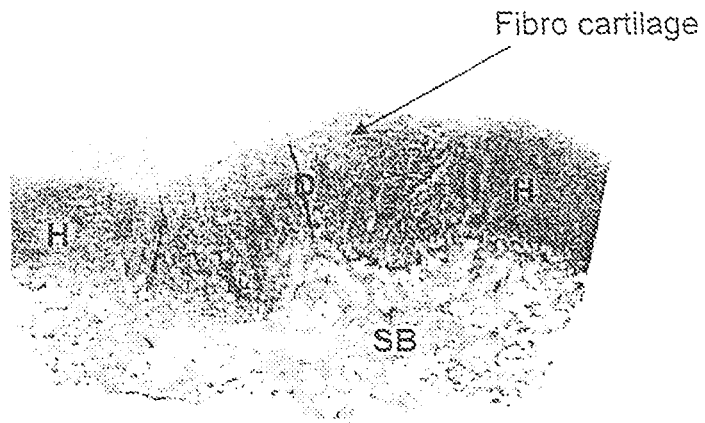
FIG. 11A shows a defect site vis-a-vis subchondral bone with a site of formation of fibrocartilage.
Figure 11B:
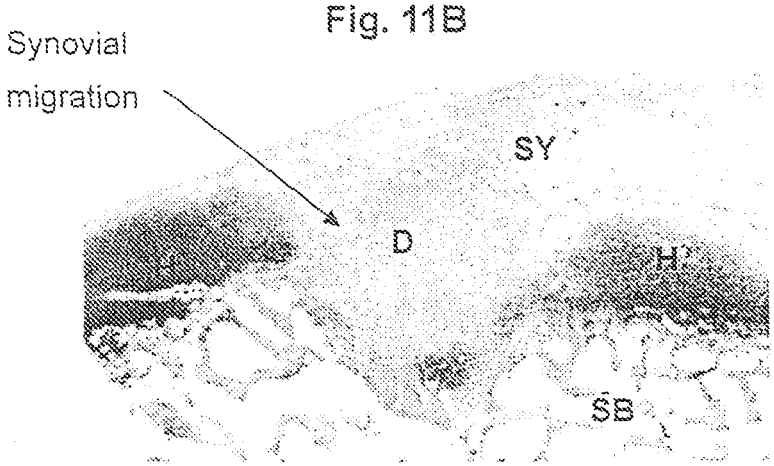
FIG. 11B shows a defect site synovium and synovial migration.
Figure 11C:
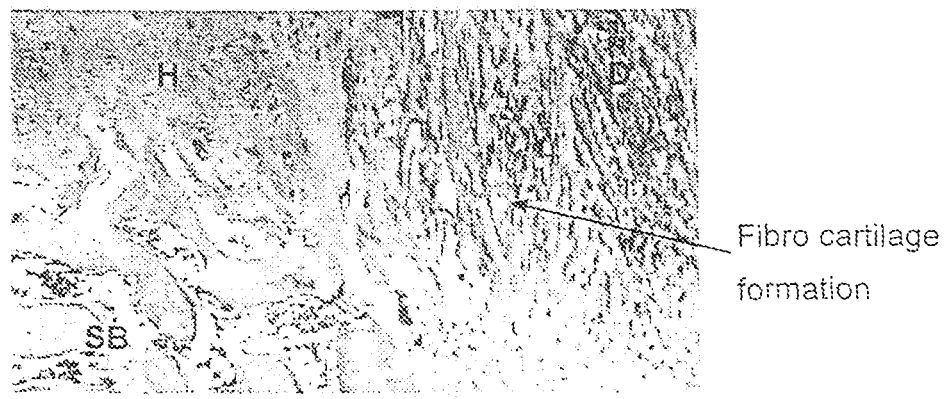
FIG. 11C shows the defect site and formation of fibrocartilage.

FIGS. 11A-11C thus shows the control lesion at 4 months following the surgery without a treatment with the neo-cartilage construct. Noticeable in FIG. 11A is the proliferation of undesirable fibrocartilage within the defect site. Also seen is synovial tissue that has infiltrated into the subchondral space.

FIGS. 12A-12D, on the other hand, show that after 3 months post implantation in a weight bearing region of the knee, the porcine neo-cartilage has produced dense hyaline-like cartilage and has integrated with the host cartilage laterally and at the interface of the subchondral bone.

Additionally, FIG. 12A shows a formation of regenerated hyaline-like cartilage in the implant site; FIG. 12B shows the beginning of integration between the porcine neo-cartilage and the native cartilage laterally and at the subchondral bone.

FIG. 12C shows already regenerated hyaline-like cartilage and FIG. 12D shows chondrocytes integration into the surrounding native cartilage.

The porcine neo-cartilage was delivered to the defect by implantation of neo-cartilage construct between two layers of sealant. The newly formed superficial cartilage layer formed over the defect at three months following the implantation is clearly visible.

FIG. 12 thus shows and confirms that 3 months after implantation in a weight-bearing region of the knee, the porcine-NeoCart™ has produced dense hyaline-like cartilage and has integrated with the host cartilage laterally and at the interface of the subchondral bone.

These results confirm that the damaged, injured, diseased or aged cartilage may be repaired by using neo-cartilage implants prepared according to the algorithm of the invention.

V. Human Osteoarthritic Cartilage

Articular cartilage is a unique tissue with no vascular, nerve, or lymphatic supply. The lack of vascular and lymphatic circulation may be one of the reasons why articular cartilage has such a poor intrinsic capacity to heal, except for formation of fibrous or fibrocartilaginous tissue. Unique mechanical functions of articular cartilage are never reestablished spontaneously after a significant injury or disease, such as osteoarthritis (OA).

In osteoarthritis, disruption of the structural integrity of the matrix by the degeneration of individual matrix proteins leads to reduced mechanical properties and impaired function.

Currently, the only available treatment of severe osteoarthritis of the knee is a total knee replacement in elderly patients. In young and middle aged patients, however, there is no optimal treatment.

In order to evaluate suitability of the current invention for treatment of osteoarthritis, studies using algorithm of the invention including a TESS culture system using neo-cartilage scaffold construct and algorithm of the invention (hydrostatic pressure and medium perfusion) on human OA chondrocytes, cell proliferation and extracellular matrix accumulation in OA chondrocytes was investigated.

Results are seen in Table 5 and in FIGS. 13-15.

TABLE 5

| | Pressure Conditions | | | | S-GAG Production | DNA content |
|---|---|---|---|---|---|---|
| | In TESS | | | | | |
| Group (n = 7) | Type of Pressure | Time | In Incubator | Total days In culture | (μg/cell construct) (Mean ± SD) | (μg/cell construct) (Mean ± SD) |
| Initial | — | — | 0 day | 0 day | 19.23 ± 0.87 | 1.88 ± 0.40 |
| Control | — | — | 21 days | 21 days | 23.81 ± 2.61 | 2.34 ± 0.32 |
| Cy-HP#1 | 0.5 MPa Cyclic | 7 days | 14 days | 21 days | *29.53 ± 1/60 | 2.33 ± 0.12 |
| Cy-HP#2 | 0.5 MPa Cyclic | 14 days | 7 days | 21 days | *34.39 ± 0.99 | 2.35 ± 0.09 |
| Const-HP | 0.5 MPa Constant | 7 days | 14 days | 21 days | 26.94 ± 5.14 | **2.65 ± 0.28 |

(*$p < 0.05$, compared to Control in S-GAG production)
(**$p < 0.05$, compared to Initial in DNA content)

In the TESS processor, the medium flow rate was 5 μl/min and the hydrostatic pressure was applied as indicated. Two cell matrices from each group were harvested for histological analysis.

Figure 13A:
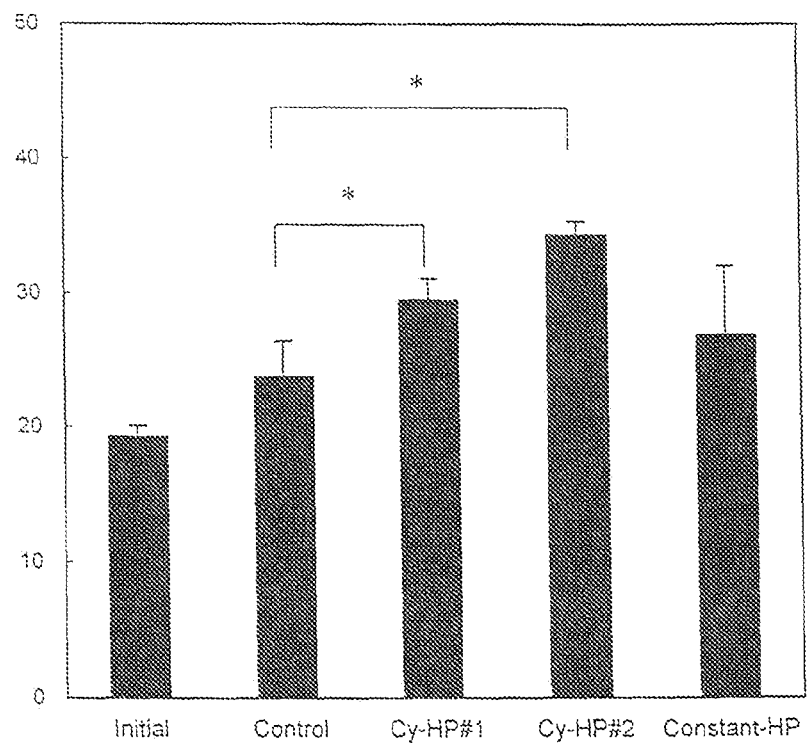
FIG. 13A shows S-GAG production in cell constructs subjected to cyclic hydrostatic pressure and to atomospheric pressure (control) with medium perfusion.

As seen in Table 5 and FIG. 13A, S-GAG production in cell constructs subjected to cyclic hydrostatic pressure with medium perfusion was significantly greater than those subjected to atmospheric pressure (control). Especially, S-GAG production (μg/cell construct) was significantly increased (144%) for Cy-HP#2 where the cyclic hydrostatic pressure was used for 14 days followed by 7 days of static atmospheric pressure compared to control.

Figure 13B:
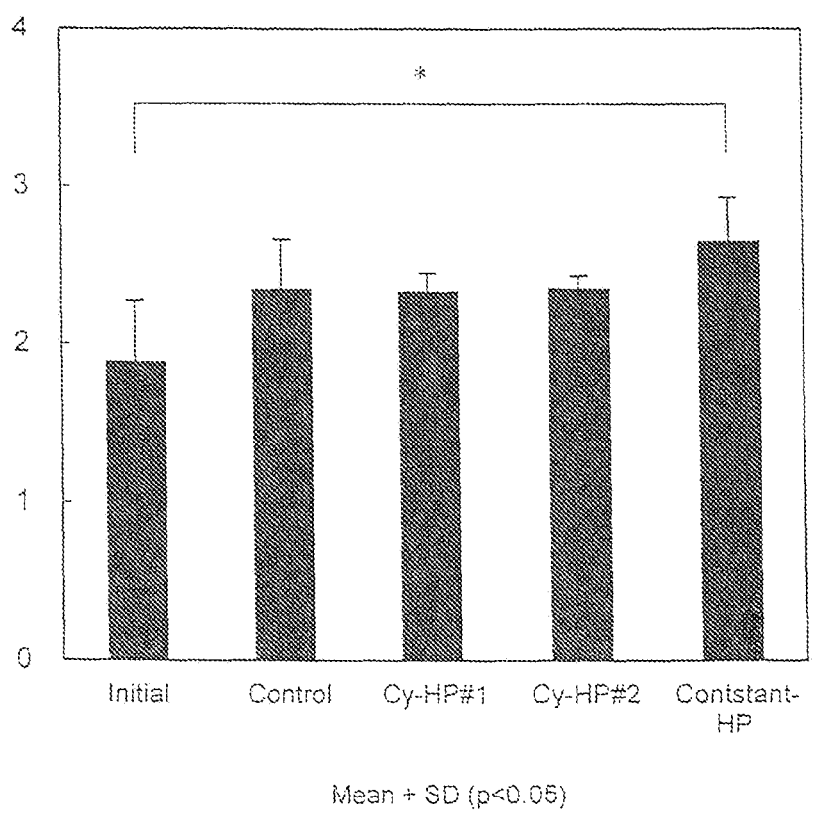
FIG. 13B shows DNA content in cell constructs subjected to cyclic and constant hydrostatic pressure with medium perfusion.

FIG. 13B shows DNA content index with corresponding results presented in Table 5 for DNA, likewise showing increased production of DNA. Increase in DNA content index in cell constructs using the neo-cartilage construct subjected to constant hydrostatic pressure was clearly shown in a comparison to initial level. DNA level in cell constructs subjected to constant hydrostatic pressure with medium perfusion was significantly increased to 142% compared to initial DNA level index.

Figure 14A:
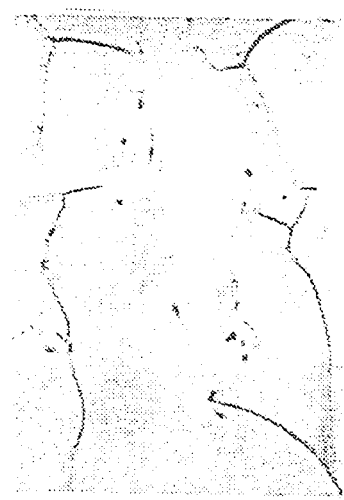
FIG. 14A shows S-GAG accumulation at day 0 (initial).
Figure 14B:
FIG. 14B shows accumulation of S-GAG on day 21 in cell constructs subjected to atmospheric pressure (control).
Figure 14C:
FIG. 14C shows accumulation of S-GAG on day 21 in cell constructs subjected to 7 days of cyclic hydrostatic pressure (Cy-HP#1) followed by 14 days of to atmospheric pressure.
Figure 14D:
FIG. 14D shows accumulation of S-GAG on day 21 in cell constructs subjected to 14 days of cyclic hydrostatic pressure (Cy-HP#2) followed by 7 days of to atmospheric pressure.
Figure 14E:
FIG. 14E shows accumulation of S-GAG on day 21 in cell constructs subjected to 7 days of constant hydrostatic pressure (Constant-HP) followed by 14 days of atmospheric pressure.

FIGS. 14A-14E show histological evaluation of cell constructs by Safranin-O. FIG. 14A shows S-GAG accumulation at day 0 (initial). FIG. 14B shows accumulation of S-GAG on day 21 in cell constructs subjected to atmospheric pressure (control). FIG. 14C shows accumulation of S-GAG on day 21 in cell constructs subjected to 7 days of cyclic hydrostatic pressure (Cy-HP#1) followed by 14 days of the atmospheric pressure. FIG. 14D shows accumulation of S-GAG on day 21 in cell constructs subjected to 14 days of cyclic hydrostatic pressure (Cy-HP#2) followed by 7 days of to atmospheric pressure. FIG. 14E shows accumulation of S-GAG on day 21 in cell constructs subjected to 7 days of constant hydrostatic pressure (Constant-HP) followed by 14 days of atmospheric pressure. The greater S-GAG accumulation in both cell constructs subjected to cyclic hydrostatic pressure (7 and 14 days) is evident from the increased density of the photomicrograph clearly visible in the FIGS. 14C and 14D.

These results demonstrate that hydrostatic pressure combined with a medium perfusion promotes both cell proliferation and neo-cartilage phenotypic activity, that is, cartilage extracellular matrix production, in the scaffold neo-cartilage constructs seeded with human OA chondrocytes. This evidence confirms that the algorithm of invention using TESS culture system and hydrostatic pressure combined with medium perfusion regenerates human OA chondrocytes and transforms the OA cartilage into the healthy hyaline cartilage.

VI. Method for Treatment of Cartilage Lesions

The method for treatment of damaged, injured, diseased or aged cartilage according to the invention is suitable for healing of small lesion due to acute injury as well as healing of the large lesions caused by osteoarthritis or other joint degenerative diseases and/or transforming the diseased OA cartilage into the healthy hyaline cartilage.

The method generally encompasses five novel features, namely, employing a biologically acceptable thermo-reversible polymer gel as a carrier support matrix for neo-cartilage generated from autologous chondrocytes, producing the autologous neo-cartilage by a process of the invention, employing a biologically acceptable thermo-reversible gel as a space-holding means for the interim period when the autologous neo-cartilage is produced, depositing one or two adhesive sealants to the lesion and, following depositing the sealants and implantation of the neo-cartilage within a cavity generated thereby, a formation of the superficial cartilage layer covering the lesion and protecting the integrity of the neo-cartilage deposited therein.

The method generally comprises steps:
a) debriding an articular cartilage lesion and during the debriding harvesting a small quantity (50-4000 mg) of non-osteoarthritic hyaline cartilage;
b) fabrication and processing of the neo-cartilage construct according to the above described procedures;
c) preparing the lesion for implantation of the neo-cartilage construct by depositing the one or two sealant layers, the first (optional) at the bottom of the lesion and the second one over and on the top of the lesion, and, using all variation already described above, depositing either the neo-cartilage construct within the cavity formed below the top sealant and/or between the two sealant layers or depositing the space holding thermo-reversible polymer gel into the cavity between the two layers to uphold the integrity of the cavity in the interim when the neo-cartilage construct is being prepared;
d) implanting the neo-cartilage construct into said cavity formed between the two sealant layers to allow for integration of the neo-cartilage into the surrounding native intact cartilage and formation of the superficial cartilage layer; and
e) optionally removing the space holding polymer gel from the cavity before the neo-cartilage implantation.

In the alternative method for treatment, expanded and differentiated chondrocytes may be deposited directly into a joint lesion in a suitable typically thermo-reversible gelation hydrogel solution.

There are several advantages of the current method. First, the method is very versatile and any of the variations may be advantageously utilized for treatment of a specific injury, damage, aging or disease.

The method permits generation of autologous neo-cartilage by providing alternative means for maintaining a space between two sealant layers until the autologous neo-cartilage is prepared. The method permits generation of more dense neo-cartilage and three-dimensional expansion of chondrocytes and extracellular matrix.

The deposition of the second top sealant layer resulting in formation of superficial cartilage layer constitutes a substitute for synovial membrane and provides the outer surface of healthy articular cartilage overgrowing, protecting, containing and providing critical metabolic factors aiding in growth and incorporation of autologous neo-cartilage in the lesion.

Deposition of the first bottom sealant layer protects the integrity of the lesion after cleaning during surgery and prevents migration of subchondral and synovial cells and cell products thereby creating milieu for formation of healthy hyaline cartilage from the neo-cartilage and also preventing formation of the fibrocartilage.

The method further permits deposition of the space-holding gel or thermo-reversible polymer gel to be deposited whether alone or with suspended processed neo-cartilage into the lesion at temperature between 5 and 30° C. as a sol. Selection of thermo-reversible gel may be crucial as certain TRGH may function as a promoter for growth of the superficial cartilage layer without a need to apply the second sealant.

The method further permits said thermo-reversible hydrogel be enhanced with hyaluronic acid, typically added in about 5 to about 50%, preferably about 20% (v/v), wherein such hyaluronic acid acts as an enhancer of the matrix-forming characteristics of the gel and to act as a hydration factor in the synovial space in general and within the lesion cavity in particular.

Additionally, the gel acts as a slow-release unit for hyaluronic acid, greatly increasing a period of hydration within the cavity and also as a substrate for formation of the superficial cartilage layer and it can also be conveniently removed, if needs be, by cooling the lesion so that the solid gel formed at 37° C. is converted to sol and can be removed by injection or otherwise.

For treatment of the cartilage, a subject is treated, according to this invention, with a prepared autologous or heterologous neo-cartilage or neo-cartilage construct implanted into the lesion, the neo-cartilage or the construct is left in the lesion for two-three months and typically, it does not need any further intervention as during these three months, the neo-cartilage is fully integrated into the native cartilage and becomes a fully functional cartilage covered with a superficial cartilage layer which eventually grows into or provides the same type of surface as a synovial membrane of the intact joint.

Finally, the diseased, osteoarthritic cartilage may be fully replaced by the regenerated hyaline-like cartilage when processed according to the algorithm of this invention.

The algorithm and/or implantation protocol may assume any variation described above or possible within the realm of this invention. It is thus intended that every and all variations in the treatment protocol (algorithm of the cartilage) are within the scope of the current invention.

Example 1

Isolation of Chondrocytes from Source Tissue

This example describes the procedure used for isolation of chondrocytes from swine cartilage.

Chondrocytes were enzymatically isolated from cartilage harvested under sterile conditions from the hind limbs of 6-month old swine. The femur was detached from the tibia and the trachea head exposed. Strips of cartilage were removed from the trachea using a surgical blade.

The cartilage was minced, digested in a 0.15% collagenase type I solution in DMEM/Nutrient Mixture F-12 (DMEM/F-12) 1:1 mixture with 1% penicillin-streptomycin (P/S) and gently rotated for 18 hours at 37° C. Chondrocytes were collected and rinsed twice by centrifugation at 1500 rpm for 5 min. Chondrocytes were re-suspended in DMEM/F-12 containing 1% penicillin-streptomysin and 10% FBS.

Chondrocytes were expanded for about 5 days at 37° C.

Example 2

The Production of Human Neo-Cartilage Construct

This example describes conditions for production of neo-cartilage for human use.

The patient undergoes arthroscopic biopsy of a small (200-500 mg) piece of healthy cartilage from the ipsilateral knee. The biopsy is taken from the non-weight bearing portion of the femoral condyle or from the femoral notch as deemed most appropriate for the patient. The biopsy sample is placed into a sterile, non-cytotoxic, non-pyrogenic specimen container which is packaged and shipped to the laboratory.

At the laboratory the biopsy sample is examined against acceptance criteria and then transferred to the chondrocyte isolation and expansion area. Samples from the biopsy specimen transport buffer are tested for sterility and for mycoplasma. The expanded chondrocytes are suspended in VITROGEN® gellable collagen solution, commercially available from Cohesion Corp., Palo Alto, Calif. A pre-formed collagen sponge (22×22 mm square and 2-4 mm in thickness, wherein the thickness depends on the thickness of patient's cartilage), commercially available from Koken Co., Japan or honeycomb matrix produced according to this invention is placed into the resulting chondrocyte suspension which absorbs the chondrocyte/collagen suspension into this matrix.

The resulting chondrocyte-loaded matrix is warmed to 37° C. to gel the VITROGEN in order to spatially secure the chondrocytes within the support matrix. The loaded support matrix is then placed into Tissue Engineering Support System (TESS™) culture unit. Typical time for cell expansion from removal of a biopsy sample to placement of the chondrocyte loaded culture matrix in the TESS™ culture unit is 10-40 days. Within the TESS™ culture unit, cyclic or constant hydrostatic pressure is used to induce the chondrocytes to begin growing and expressing their cartilage generating program for about 1 hour to about 30 days.

The still developing new cartilage is transferred to a constant, resting culture phase. The neo-cartilage production process requires a minimum time of 10 days in resting culture. After this minimum 10-day period the neo-cartilage, hereinafter called neo-cartilage construct, undergoes final inspections and is packaged for return to the clinic to be implanted. At the time of release, tests for sterility, endotoxin, and mycoplasma contamination must be negative for microbial and mycoplasma contamination and must show ≤0.5 EU/ml of endotoxin.

Example 3

Preparation of Support Matrices

This example illustrates preparation of the cellular support matrix, also called the TESS matrix.

300 grams of a 1% aqueous atelocollagen solution) (VITROGEN®, maintained at pH 3.0, is poured into a 10×20 cm tray. This tray is then placed in a 5 liter container. A 50 ml open container containing 30 ml of a 3% aqueous ammonia solution is then placed next to the tray, in the 5 liter chamber, containing 300 grams of said 1% aqueous solution of atelocollagen. The 5 liter container containing the open trays of atelocollagen and ammonia is then sealed and left to stand at room temperature for 12 hours. During this period the ammonia gas, released from the open container of aqueous ammonia and confined within the sealed 5 liter container, is reacted with the aqueous atelocollagen resulting in gelling said aqueous solution of atelocollagen.

The collagenous gel is then washed with water overnight and, subsequently, freeze-dried to yield a sponge like matrix. This freeze dried matrix is then cut into squares, sterilized, and stored under a sterile wrap.

Alternatively, the support matrix may be prepared as follows.

A porous collagen matrix, having a thickness of about 4 mm to 10 mm, is hydrated using a humidity-controlled chamber, with a relative humidity of 80% at 25° C., for 60 minutes. The collagen material is compressed between two Teflon sheets to a thickness of less than 0.2 mm. The compressed material is then cross-linked in a solution of 0.5% formaldehyde, 1% sodium bicarbonate at pH 8 for 60 minutes. The cross-linked membrane is then rinsed thoroughly with water, and freeze-dried for about 48 hours. The dense collagen barrier has an inner construction of densely packed fibers that are intertwined into a multi-layer structure.

In alternative, the integration layer is prepared from collagen-based dispersions or solutions that are air dried into sheet form. Drying is performed at temperatures ranging from approximately 4 to 40° C. for a period of time of about 7 to 48 hours.

Example 4

Seeding Cells in the TESS Matrix

This example describes procedures used for seeding cells in the TESS matrix.

Isolated chondrocytes were incubated for a period of five days at 37° C. in a standard incubator. Cells were then collected by trypsinization.

A cell suspension of 150,000 cells in 18 µl of VITROGEN solution was seeded per matrix having an approximate volume of 19 µl, with nine matrices per group. The seeded matrix (collagen sponge 4 mm in diameter and 1.5 mm in thickness) may be scaled-up to an increased volume, where approximately 1 µl of the above described cell suspension is seeded in 1 µl of matrix. The control group matrices were incubated in a 37° C. incubator and the test group was incubated in the TESS.

In alternative set-up, isolated chondrocytes were incubated for a period of five days at 37° C. in a standard incubator. Cells were then collected by trypsinization. A cell suspension of 300,000 cells in 18 µl of VITROGEN solution was seeded per matrix having an approximate volume of 19 µl with eight matrices per group.

Example 5

Effect of Cyclic Hydrostatic Pressure

This example describes procedures used for determination of effect of cyclic hydrostatic pressure in vitro formation of chondrocyte-seeded support matrices.

Swine articular chondrocytes (sACs) were enzymatically isolated from cartilage with type I collagenase. The cells were suspended in collagen (VITROGEN) as described above and wicked into the honeycombed sponge element of the cellular support matrix. The cells seeded in the support matrix were incubated at 37° C., 5% $CO_2$ and 20% $O_2$. After 24 hours, some of these cells matrices were transferred to the TESS™ processor and incubated at 0.5 or 3.0 MPa cyclic or constant hydrostatic pressure with medium perfusion (0.05 ml/min) as described above for 6 or 7 days followed by a 12 or 14 day resting phase. The control group comprised of chondrocytes seeded in matrices incubated for 18 or 21 days at atmospheric pressure, at 37° C., 5% $CO_2$ and 20% or 2% $O_2$.

At the end of the culture period (18 or 21 days), the matrices were harvested for biochemical and histological analysis. For biochemical analysis, sulfated glycosaminoglycan (S-GAG) production was measured using a modified dimethylmethylene blue (DMB) microassay.

Two matrices from each group were harvested for histological analysis.

Example 6

Effect of Medium Flow Rate on Extracellular Matrix Accumulation of Chondrocytes in Collagen Sponges This example described conditions used to determine effect of medium flow on production and accumulation of extracellular matrix by chondrocytes seeded into collagen sponges.

Chondrocyte Isolation

Swine legs were obtained from a local abattoir. Within 4-6 hours after slaughter, cartilage was harvested under sterile conditions from the trochlea of the hind limbs. The cartilage was minced and digested in 0.15% collagenase type I in DMEM/F-12 containing 1% penicillin-streptomycin (P/S) for 18 hours at 37° C. Isolated swine articulate chondrocytes (sACs) were collected, rinsed, and resuspended in DMEM/F-12 supplemented with 10% fetal bovine serum (FBS) and 1% P/S. sACs then were expanded for 5 days at 37° C.

Cell Seeding in Collagen Sponges sACs were harvested with Trypsin EDTA and cell viability was measured by trypan-blue exclusion. Three hundred thousand sACs were suspended in 30 µl of a neutralized 0.25% collagen solution (VITROGEN®, Cohesion Corp., Palo Alto, Calif.), and the suspension was absorbed into a collagen sponge, 4 mm in diameter and 2 mm in thickness, commercially available from Koken Co., Japan. Seeded sponges were pre-incubated for 1 hour at 37° C. to gel the collagen, followed by incubation in culture medium at 37° C. in 5% $CO_2$.

Tissue Engineering Support System (TESS™) Culture

Following the incubation, the seeded sponges were transferred to and cultured in the Tissue Engineering Support System (TESS™) processor. To evaluate the effect of medium perfusion rate, sponges were subjected to medium perfusion at 5 µl/min or 50 µl/min. Cyclic hydrostatic pressure (Cy-HP) 0-0.5 MPA pressure at 0.5 Hz applied was for 6 days. Some sponges were incubated under constant conditions at atmospheric pressure and no perfusion at 37° C. for a total of 18 days in culture. Sponges harvested 24 hours after seeding with cells (day 0) served as an initial control.

Histological and Biochemical Analysis

Cell constructs were harvested after 6 and 18 days of culture.

For histological evaluation, 4% paraformaldehyde-fixed, paraffin sections were stained with Safranin-O (Saf-O) and Type II collagen antibody.

For biochemical analysis, seeded sponges were digested in papain at 60° C. for 18 hours and DNA content was measured using the Hoechst 33258 dye method. Sulfated glycosaminoglycan (S-GAG) accumulation was measured using a modified dimethylmethylene blue (DMB) microassay.

Example 7

Biochemical and Histological Assays

This example describes assays used for biochemical and histological studies (DMB assay).

Biochemical (DMB) Assay

At the end of the culture six matrices from each group were used in the biochemistry assay.

The matrices were transferred to microcentrifuge tubes and digested in 300 µl of papain (125 µg/ml in 0.1 M sodium phosphate, 5 mM disodium EDTA, and 5 mM L-cysteine-HCl) for 18 hours at 60° C. GAG production in the matrices was measured using a modified dimethylene blue (DMB) microassay with shark chondroitin sulfate as a control *Connective Tissue Research*, 9: 247-248 (1982).

DNA content was determined by Hoechst 33258 dye method according to *Anal. Biochem.*, 174:168-176 (1988).

Histological Assay

The remaining matrices from each group were fixed in 4% paraformaldehyde. The matrices were processed and embedded in paraffin. 10 µm sections were cut on a microtome and stained with Safranin-O (Saf O).

Example 8

Evaluation of Porcine Neo-Cartilage Integration in a Swine Model

This example describe the procedure and results of study performed for evaluation of integration of porcine neo-cartilage in a swine model.

An open arthrotomy of the right knee joint was performed on all animals, and a biopsy of the cartilage was obtained.

Chondrocytes were isolated from the cartilage biopsy and cultured within a collagen matrix in a Tissue Engineering Support System (TESS™) to produce porcine-Neocart for subsequent implantation.

A defect was created in the medial femoral condyle of the pig's right knee. This defect (control) was not implanted with porcine-NeoCart™. Following surgery, the joint was immobilized with an external fixation construct for a period of about two weeks. Three weeks after the arthrotomy on the right knee was performed, an open arthrotomy was performed on the left knee and defects were created in this medial femoral condyle. The porcine-NeoCart™ was implanted within the defect (s) in this knee which was similarly immobilized. The operated sites were subsequently viewed via arthroscopy two weeks after implantation or defect creation and thereafter at monthly intervals. Animals were euthanized and the joints harvested and prepared for histological examination approximately 3 months after porcine-NeoCart™ implantation. The implanted sites were prepared and examined histologically.

Results are seen in FIGS. 10-12. FIG. 10 shows results of the arthroscopic examination. The empty defect is seen in FIG. 10A. The porcine NeoCart™ implant site is seen in FIG. 10B which also shows still-evident absorbable sutures and the superficial cartilage layer growing over the porcine NeoCart™.

Example 9

Protocol for In Vivo, Ex Vivo or In Vitro Growth of Porcine Neo-Cartilage

Autologous porcine chondrocytes are seeded into the cellular support matrix and incubated under cyclic hydrostatic pressure at 37° C. and 5% $CO_2$. Cyclic hydrostatic pressure is either 0.5 or 3.0 MPa at 0.5 Hz. The duration of said cyclic pressure is approximately 6 days followed by a resting phase of 12 days in an incubator maintained at 37° C. at atmospheric pressure. At the end of this resting phase, the matrices were harvested for biochemical and histological analysis.

In the alternative protocol, the algorithm for the growth cells of in vivo and in vitro, the application of hydrostatic pressure is used on isolated in situ cartilage, or application of hydrostatic pressure for about 1-8 hours followed by about 16-23 hours of recovery period.

Example 10

Regeneration of Human Chondrocytes

This example describes the procedure used for regeneration of human chondrocytes.

Chondrocytes from osteoarthritic (OA) patients (40 years old) were expanded for 18 days in monolayer culture at 37° C. and suspended in VITROGEN® (300,000 cells/30 fÊl). The cell suspension was absorbed into a support matrix, usually a collagen honeycomb sponge (4 mm in diameter and 2 mm in thickness, Koken Co., Japan). The cell constructs were incubated in culture medium supplemented with 10% FBS and 1% ITS (insulin-transferrin-sodium selenite, Sigma) at 37° C., 5% $CO_2$ and 20% $O_2$, at 0.5 MPa cyclic hydrostatic pressure (Cy-HP) or 0.5 MPa constant hydrostatic pressure (Constant-HP) for 7 or 14 days in the TESS™ processor followed by incubation for 7 or 14 days at atmospheric pressure for 7 or 14 days in an $CO_2$ incubator at 37° C. The remaining cell constructs compromising the control group were incubated atmospheric pressure for 21 days at 37° C., 5% $CO_2$ and 20% $O_2$.

Before starting the culture, some cell constructs were harvested for biochemical and histological analysis as an initial condition. At the end of the culture period, the cell constructs were harvested for biochemical and histological analysis. Sulfated glycosaminoglycan production was measured using a modified dimethylmethylene blue (DMB) micro assay. Cell proliferation was measured using a modified Hoechst Dye DNA assay. Formation of neo-tissue was analyzed by Safranin-O Staining.

What is claimed:

1. A method for preparing a neo-cartilage construct, said method comprising the steps of:
   providing a lyophilized acellular matrix comprising a plurality of pores;
   seeding said acellular matrix with a plurality of chondrocytes; and
   culturing said seeded matrix under conditions that comprise:
   applying cyclic hydrostatic pressure from about 0.5 MPa to about 3 MPa above atmospheric pressure, at a frequency of about 0.1 Hz to about 2.0 Hz, for about 6 days to about 14 days followed with a resting period at atmospheric pressure for about 7 days to about 28 days; and
   said neo-cartilage construct is obtained.

2. The method of claim 1, wherein the acellular matrix further comprises at least one bioactive agent selected from the group consisting of a growth factor, a cytokine, a peptide, and a combination thereof.

3. The method of claim 1, further comprising the step of implanting said seeded matrix into a cartilage lesion of a subject.

4. The method of claim 3, wherein said chondrocytes are autologous or heterologous.

5. The method of claim 3, wherein a tissue sealant is used to implant the seeded matrix into the cartilage lesion in said subject.

6. The method of claim 5, wherein said tissue sealant is deposited into the cartilage lesion before the seeded matrix is implanted therein.

7. The method of claim 5, wherein said tissue sealant is deposited over the seeded matrix after implantation into the cartilage lesion in said subject.

8. The method of claim 5, wherein said tissue sealant is selected from the group consisting of gelatin, a copolymer of polyethylene glycol and poly-lactide or poly-glycolide, periodate-oxidized gelatin, 4-armed pentaerythritol thiol and a polyethylene glycol diacrylate, 4-armed tetra-succinimidyl ester or tetra-thiol derivatized PEG, photo-polymerizable polyethylene glycol-co-poly(α-hydroxy acid)diacrylate macromer, 4-armed polyethylene glycol derivatized with succinimidyl ester and thiol further cross-linked with methylated collagen, derivatized polyethylene glycol (PEG), polyethylene glycol (PEG) cross-linked with alkylated collagen, tetrahydrosuccinimidyl or tetra-thiol derivatized PEG, PEG cross-linked with methylated collagen, and a combination thereof.

* * * * *